United States Patent
Köppel et al.

(10) Patent No.: US 11,793,921 B2
(45) Date of Patent: Oct. 24, 2023

(54) REPLACEMENT PART FOR OPHTHALMOLOGICAL APPARATUS

(71) Applicant: THIS AG, Heerbrugg (CH)

(72) Inventors: Thomas Köppel, Widnau (CH); Marco Zünd, Widnau (CH); Martin Christoph Heiss, Appenzell Eggerstanden (CH)

(73) Assignee: THIS AG, Heerbrugg (CH)

( * ) Notice: Subject to any disclaimer, the term of this patent is extended or adjusted under 35 U.S.C. 154(b) by 1077 days.

(21) Appl. No.: 16/347,459

(22) PCT Filed: Nov. 2, 2017

(86) PCT No.: PCT/EP2017/078073
§ 371 (c)(1),
(2) Date: May 3, 2019

(87) PCT Pub. No.: WO2018/083182
PCT Pub. Date: May 11, 2018

(65) Prior Publication Data
US 2019/0255231 A1     Aug. 22, 2019

(30) Foreign Application Priority Data
Nov. 3, 2016   (EP) ..................................... 16197018

(51) Int. Cl.
*A61M 1/00*       (2006.01)
*A61F 9/007*      (2006.01)
(Continued)

(52) U.S. Cl.
CPC ............... *A61M 1/72* (2021.05); *A61F 9/007* (2013.01); *A61F 9/00736* (2013.01);
(Continued)

(58) Field of Classification Search
CPC ...... A61F 9/007; A61F 9/00709; A61F 9/013; A61M 1/72; A61M 2205/12;
(Continued)

(56) References Cited

U.S. PATENT DOCUMENTS

| | | | |
|---|---|---|---|
| 3,815,604 | A | 6/1974 | O'Malley et al. |
| 3,841,157 | A | 10/1974 | Willock |

(Continued)

FOREIGN PATENT DOCUMENTS

| | | |
|---|---|---|
| CN | 1292084 A | 4/2001 |
| CN | 101045026 A | 10/2007 |

(Continued)

OTHER PUBLICATIONS

International Search Report and Written Opinion dated Jan. 15, 2018 in International Application No. PCT/EP2017/078073.

*Primary Examiner* — Erich G Herbermann
*Assistant Examiner* — Seth Han
(74) *Attorney, Agent, or Firm* — Muncy, Geissler, Olds & Lowe, P.C.

(57) ABSTRACT

The invention relates to a replaceable cartridge (1) for an ophthalmological apparatus (2), comprising at least one hard region as a housing and at least one soft region, the hard region and the soft region forming inner liquid channels of the replacement cartridge (1). The soft region embodies functional elements of the replacement cartridge (1), said functional elements comprising at least one pump device for pumping liquid into the liquid channels, a valve device for modifying a through-flow cross-section in at least one of the liquid channels, and a pressure-detecting device for determining a liquid pressure in at least one of the liquid channels. The pressure-detecting device comprises a pressure chamber which is connected to one of the liquid channels, and a flexible membrane which peripherally sur- (Continued)

rounds a coupling element. The coupling element is designed with a recess such that a fork-shaped arm of a force-measuring device, which is oriented substantially parallel to the membrane, can be inserted into the recess in such a way that the coupling element has at least two sides, and with the arm, a force effect occurring in a substantially normal direction in relation to the membrane can be detected on the membrane.

19 Claims, 7 Drawing Sheets

(51) Int. Cl.
*G01L 19/00* (2006.01)
*G01L 13/02* (2006.01)

(52) U.S. Cl.
CPC ........... *A61F 9/00745* (2013.01); *A61M 1/77* (2021.05); *A61M 1/772* (2021.05); *G01L 13/025* (2013.01); *G01L 19/0023* (2013.01); *A61M 2205/12* (2013.01); *A61M 2205/121* (2013.01); *A61M 2205/3331* (2013.01); *A61M 2207/00* (2013.01)

(58) Field of Classification Search
CPC .... A61M 2205/121; A61M 2205/3331; A61M 2205/3351; A61M 2205/3355; A61M 1/73; G01L 13/025; G01L 19/0023; G01L 19/003
See application file for complete search history.

(56) References Cited

U.S. PATENT DOCUMENTS

| | | |
|---|---|---|
| 3,934,543 A | 1/1976 | Howard |
| 4,034,610 A | 7/1977 | Montgomery et al. |
| 4,161,887 A | 7/1979 | Stone et al. |
| 4,637,813 A | 1/1987 | Devries |
| 4,890,497 A | 1/1990 | Cahill |
| 5,163,900 A | 11/1992 | Wortrich |
| 5,252,826 A | 10/1993 | Kemp |
| 5,282,787 A | 2/1994 | Wortrich |
| 5,360,398 A | 11/1994 | Grieshaber et al. |
| 5,364,342 A | 11/1994 | Beauchat |
| 5,392,653 A | 2/1995 | Zanger et al. |
| 5,454,783 A | 10/1995 | Grieshaber et al. |
| 5,582,601 A | 12/1996 | Wortrich |
| 5,746,719 A | 5/1998 | Farra |
| 5,800,396 A | 9/1998 | Fanney |
| 5,897,524 A | 4/1999 | Wortrich |
| 5,899,674 A | 5/1999 | Jung |
| 6,058,779 A | 5/2000 | Cole |
| 2002/0107468 A1 | 8/2002 | Chevallet et al. |
| 2003/0190244 A1 | 10/2003 | Davis |
| 2008/0114301 A1 | 5/2008 | Bandhauer et al. |
| 2008/0200878 A1 | 8/2008 | Davis et al. |
| 2010/0152647 A1* | 6/2010 | Shener .................. A61M 3/022 137/561 R |
| 2013/0245543 A1* | 9/2013 | Gerg ........................ A61B 3/16 604/30 |
| 2013/0303978 A1 | 11/2013 | Ross |
| 2013/0330208 A1* | 12/2013 | Ly ......................... F04B 17/042 417/413.1 |
| 2016/0045367 A1 | 2/2016 | Horvath |
| 2020/0054802 A1 | 2/2020 | Köppel |

FOREIGN PATENT DOCUMENTS

| | | |
|---|---|---|
| CN | 101229397 A | 7/2008 |
| CN | 101472626 A | 7/2009 |
| CN | 101727125 A | 6/2010 |
| CN | 201508264 U | 6/2010 |
| CN | 104697699 A | 11/2019 |
| DE | 69309757 T2 | 8/1997 |
| DE | 69316209 T2 | 7/1998 |
| DE | 69321264 T2 | 2/1999 |
| DE | 102009037845 A1 | 4/2001 |
| DE | 69615507 T2 | 5/2002 |
| DE | 69615633 T2 | 7/2002 |
| DE | 69709192 T2 | 8/2002 |
| DE | 69621562 T2 | 1/2003 |
| DE | 60000608 T2 | 6/2003 |
| EP | 1253412 A2 | 10/2002 |
| EP | 3318226 A1 | 5/2018 |
| FR | 2273259 A1 | 10/1976 |
| FR | 2463923 A1 | 2/1981 |
| JP | H07507461 A | 12/1993 |
| JP | 2002233570 A | 8/2020 |
| WO | 1987001943 A1 | 4/1987 |
| WO | 1993024082 A1 | 12/1993 |
| WO | 2002028449 A2 | 4/2002 |
| WO | 2002056850 A1 | 7/2002 |
| WO | 2004108189 A2 | 12/2004 |
| WO | 2004110524 A2 | 12/2004 |
| WO | 2006065790 A1 | 6/2006 |
| WO | 2010129128 A1 | 11/2010 |
| WO | 2015009945 U | 1/2015 |

* cited by examiner

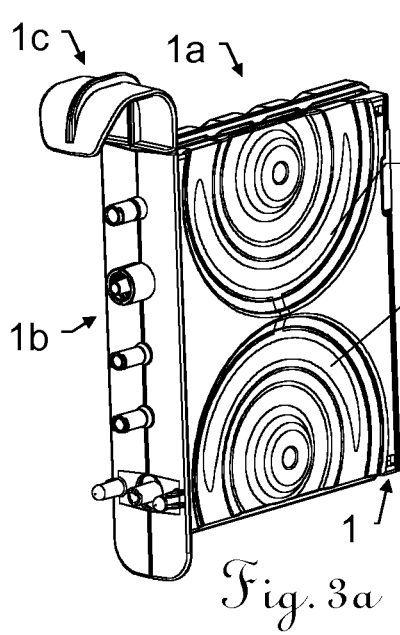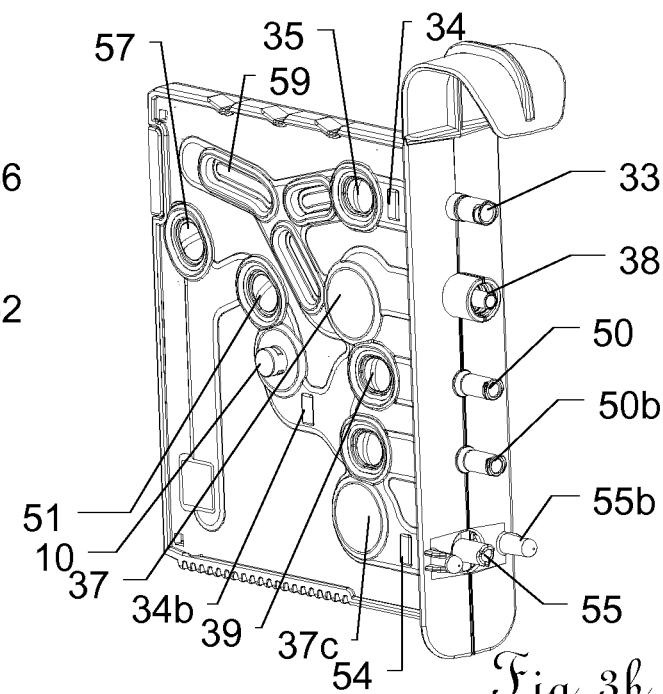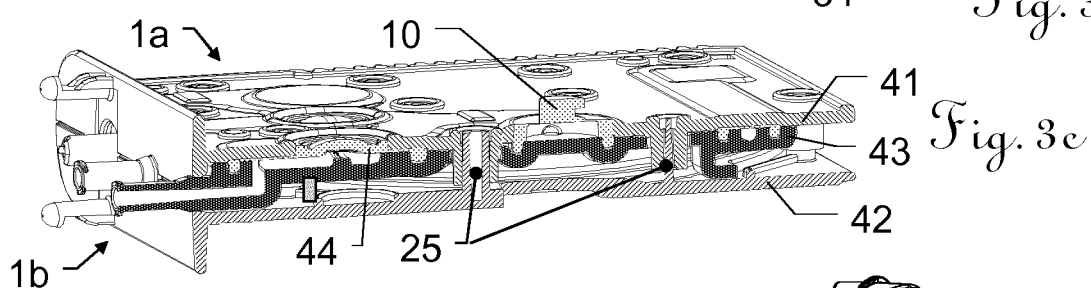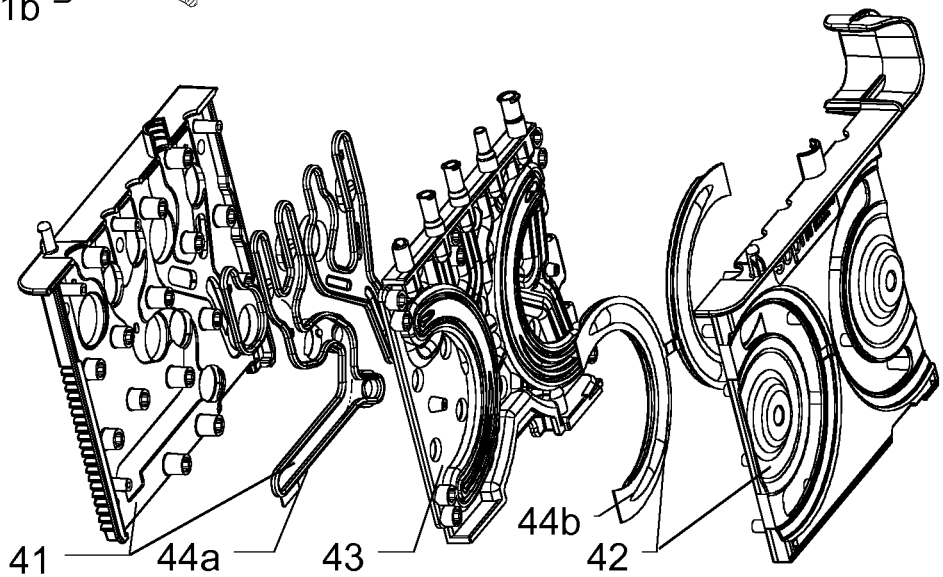

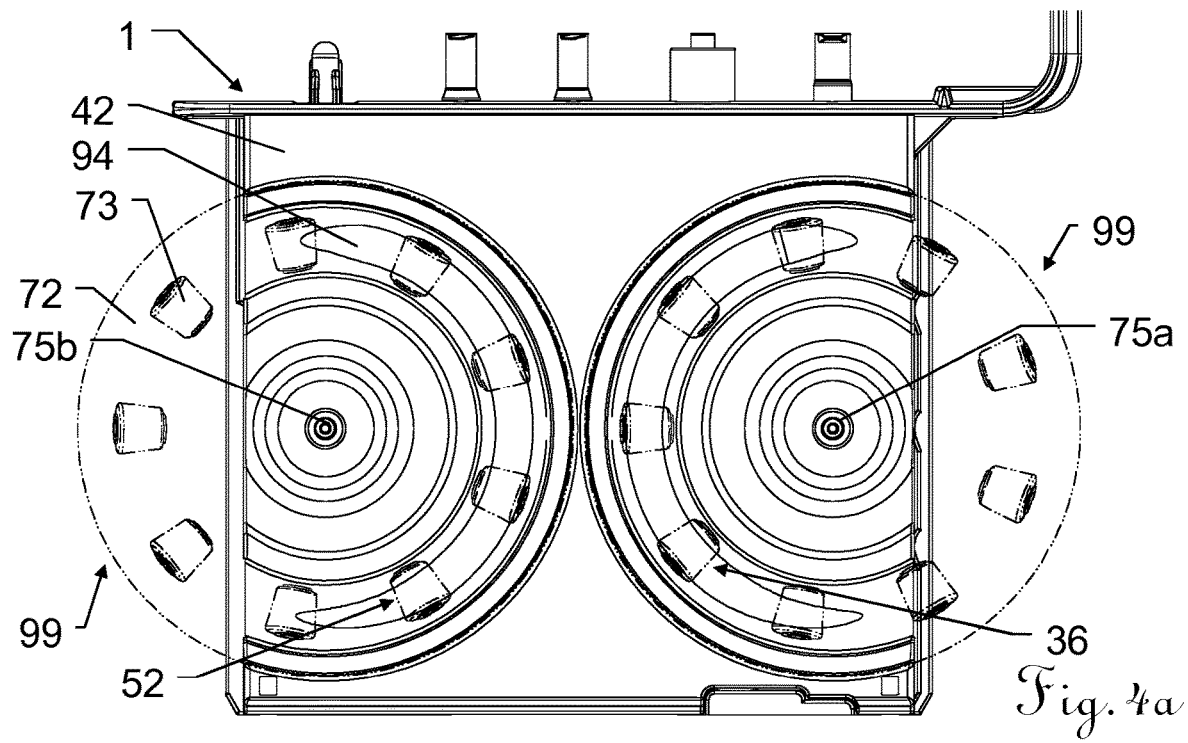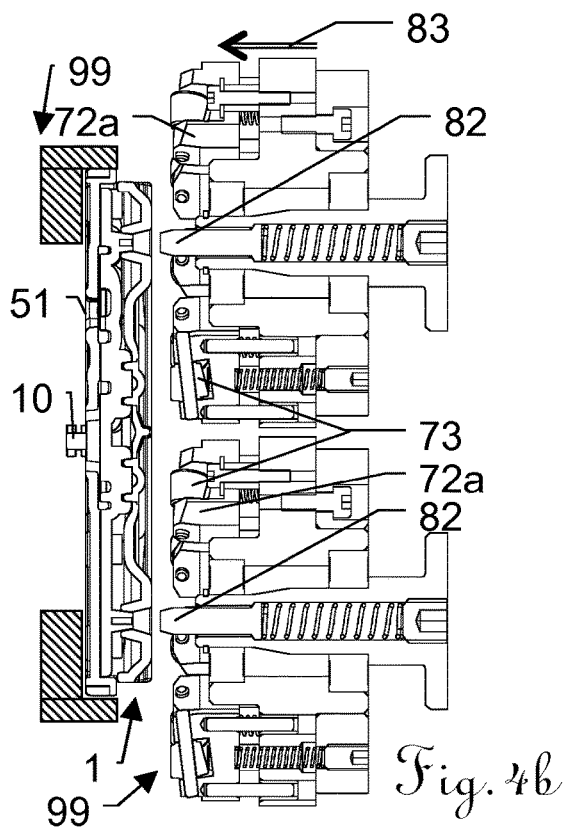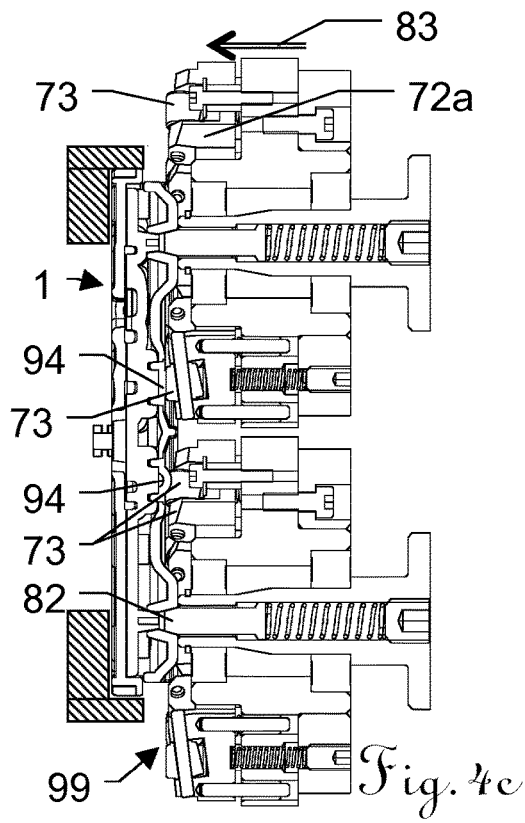

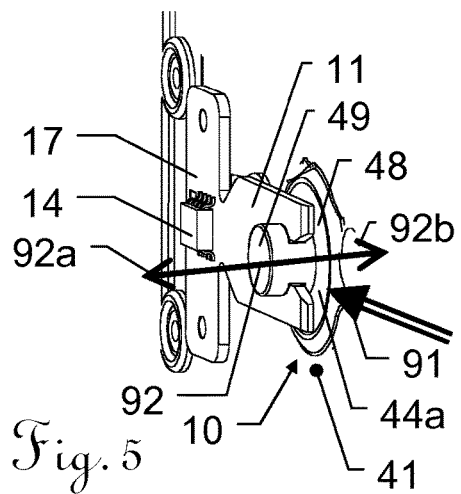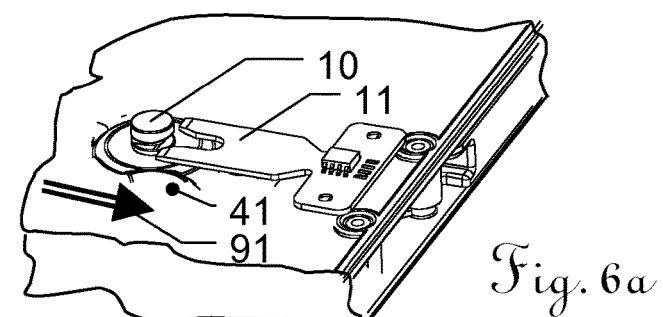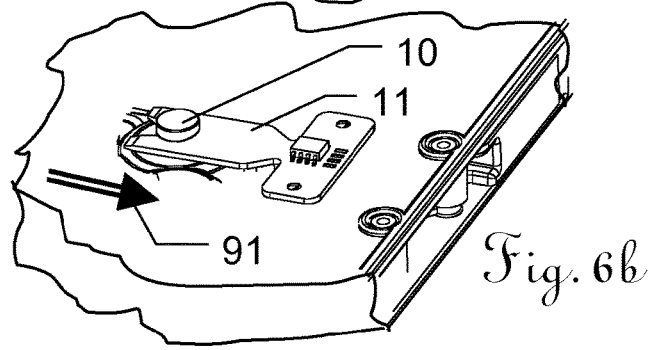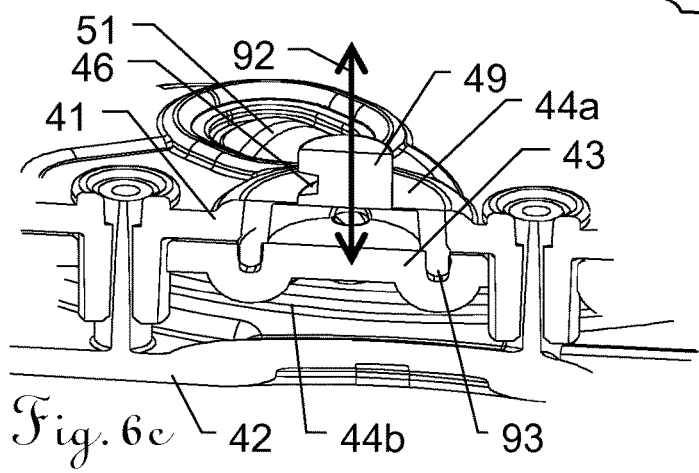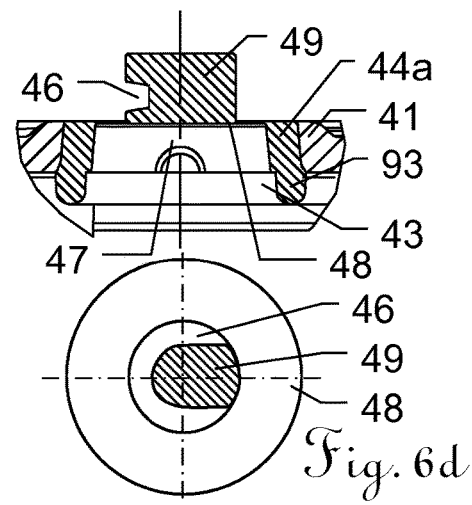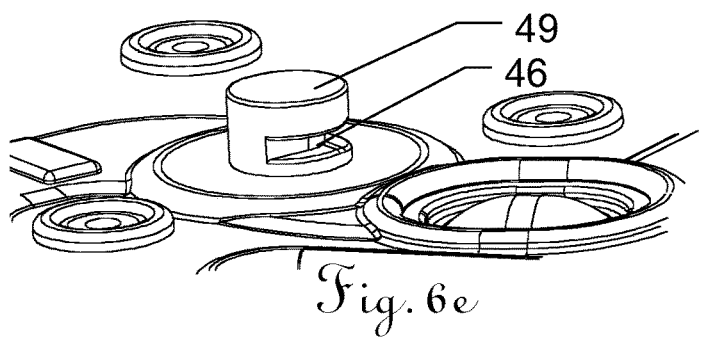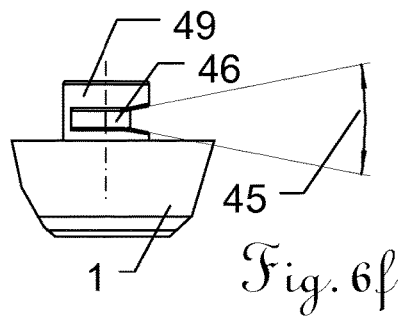

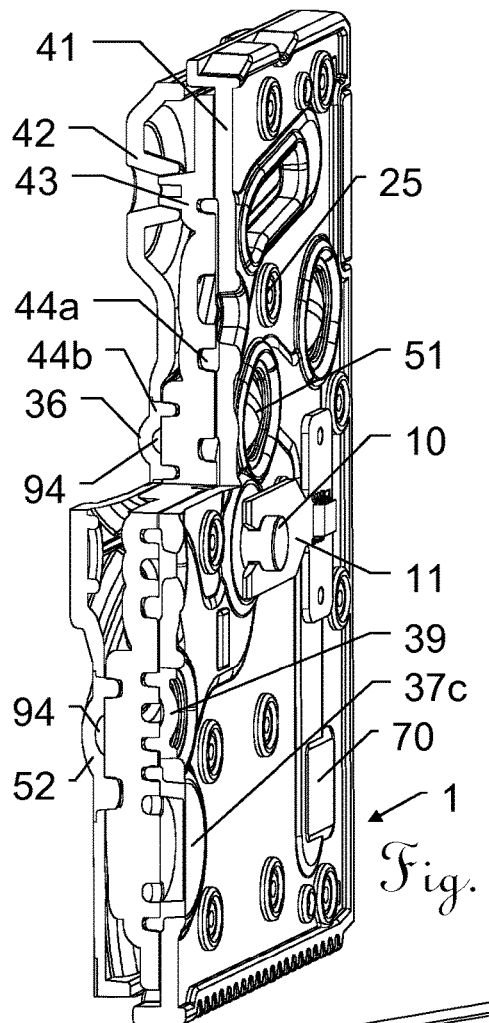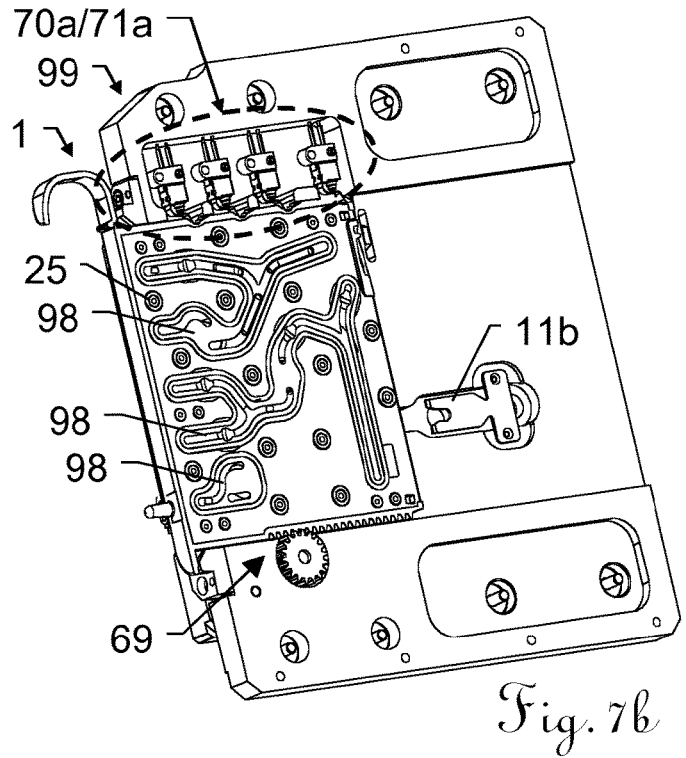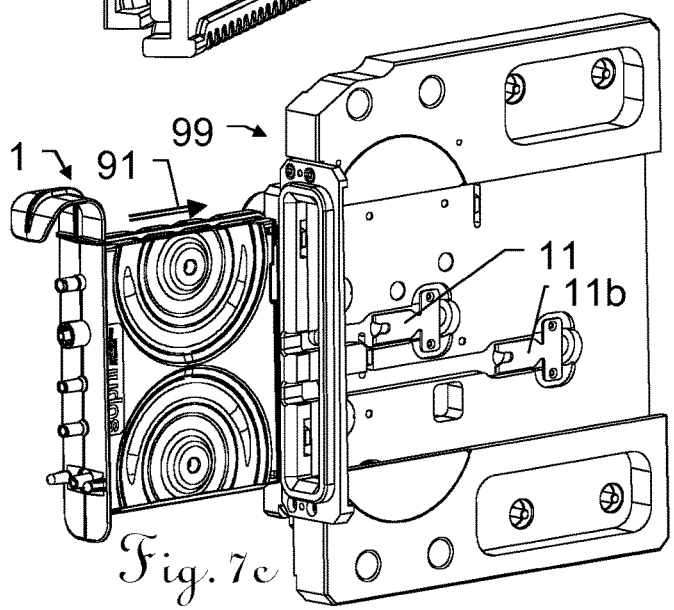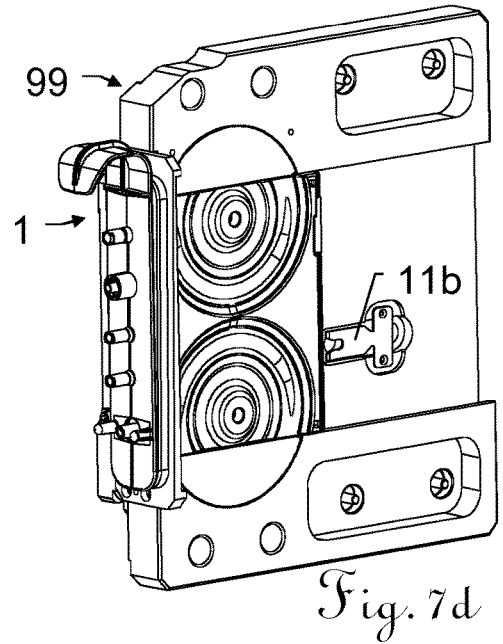

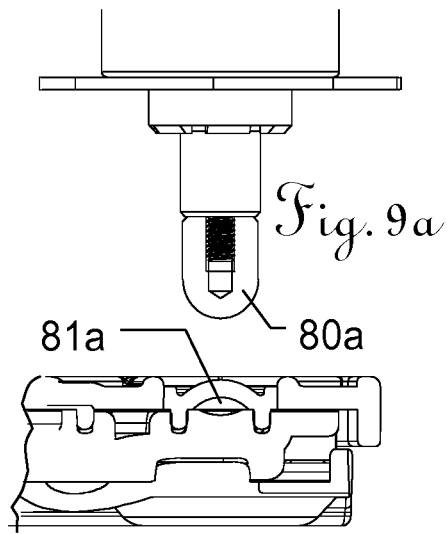
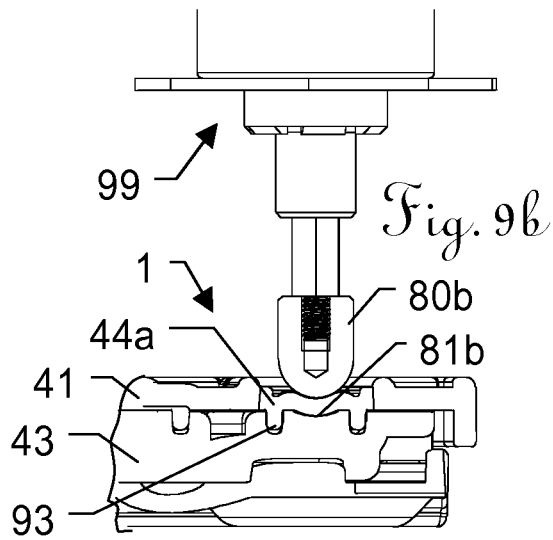
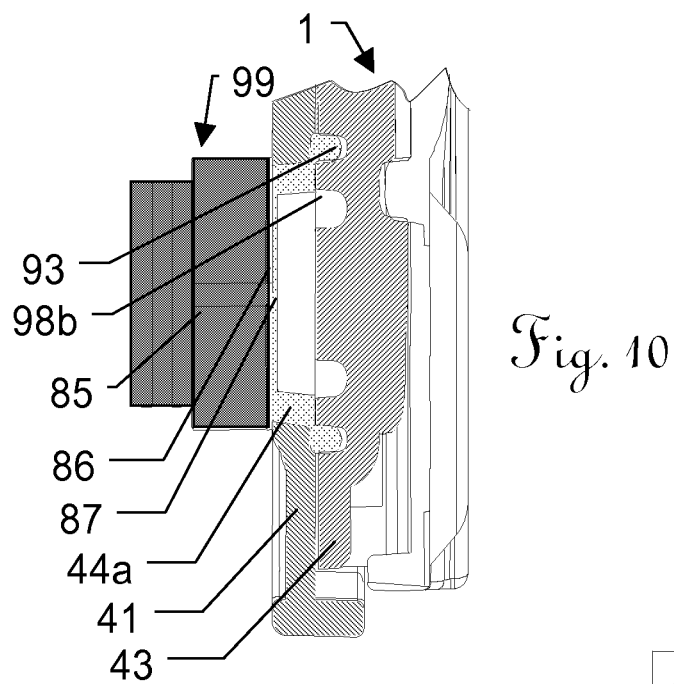
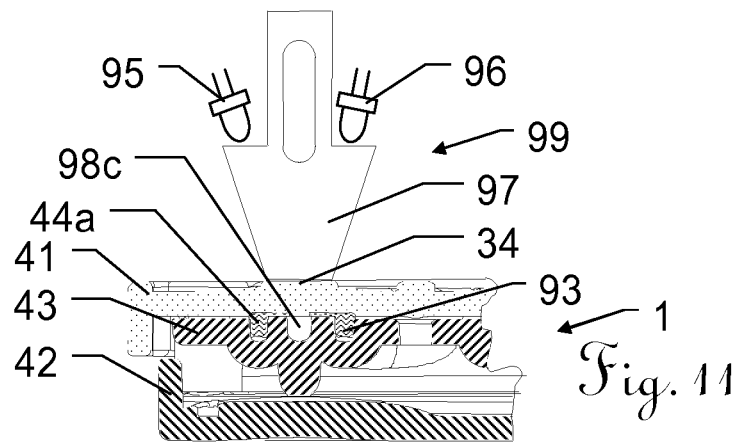

REPLACEMENT PART FOR OPHTHALMOLOGICAL APPARATUS

This application is a 371 National Phase of PCT Application No. PCT/EP2017/078073, filed on Nov. 2, 2017; which claims priority to European Patent application 16197018.1 filed Nov. 3, 2016 and each of which is herein incorporated by reference in its entirety.

The invention relates to a replacement part for an opthalmological apparatus according to the preamble of claim 1 and to an associated device according to claim 10, and to a method for measuring pressure, for producing a coupling of the pressure measurement, and for producing the replacement part.

The invention relates to ophthalmic surgical apparatuses. In many cases, aspiration, i.e. the suction of eye fluid or particles removed during surgery, takes place during interventions inside the eye. For example, during cataract surgery, the clouded lens is removed from the eye and replaced by an intraocular lens (IOL).

In the case of cataract surgery, which is performed frequently, a phacoemulsification (liquefaction of the lens nucleus) is performed in which, for example, surgical tools are inserted into the interior of the eye via an incision a few millimeters long in the area of the transition from the cornea to the dermis. A piece of the capsule is removed and then the lens contents are crushed and removed, for example with an ultrasound device or laser. The lens particles are removed by means of suction flushing connected to the surgical tool, which is a core element of the present invention. This suction flushing, which is usually designed as part of an operating device with other functions required for the surgical procedure, aspirates the shattered lens nucleus particles and replaces the aspirated material with liquid infusion, for example with a Balanced Salt Solution (BSS). After removing the old lens core, a folded, elastic replacement lens is inserted into the capsular bag through the opening.

In addition to the phacoemulsification described above, the same medical devices with suction flushing function that are treated by this invention (or specific versions of such devices) are also used in other ophthalmological procedures in which an interocular aspiration or an infusion or both are often (but not necessarily) performed, for example in vitrectomy, diathermy, capsulotomy, glaucoma surgery, refractive surgery, femto-laser, etc.

Documents DE 696 21 562, US 2016/045367, WO 02/056850 describe exemplary embodiments of such medical equipment.

For the suction flushing function, i.e. for infusion and/or aspiration, an appropriate medical device is provided, which provides the supply and discharge of the fluids, as well as any other functions such as the control of phacoemulsification. For this purpose, the surgical device used to intervene in the eye is equipped with an aspiration line for aspiration and an infusion line to replace the aspirated liquid and/or leaking liquid emerging through the insertion opening. In particular, the eye pressure (IOP=Inter Ocular Pressure) must be kept at least approximately constant during the operation so that the eye, or an eye part such as the anterior chamber, neither collapses nor is inflated during the procedure, and therefore, parallel to the suction by aspiration, an infusion, i.e. supply of liquid, thus takes place at the same time.

In order to ensure sterility, intraocular infection or transmission from patient to patient must be safely avoided, especially with regard to aspirated which is potentially contaminated. This can be achieved, for example, by replacing a replacement insert, which is usually referred to as a cassette. These cassettes can be designed as disposable cassettes, daily cassettes and/or multiple sterilizable. In particular, the cassette provides the aspiration effect and contains in particular those parts which come or could come into contact with potentially contaminated patient fluid. These parts can be especially pump or suction apparatuses, valves and/or sensors for pressure and vacuum, air bubbles, flow, etc. Connections—preferably mechanically coded to prevent confusion—to lines to and/or from the patient, as well as for connections for waste and/or infusion containers, etc., are also usually part of such an interchangeable cassette, which is at least partially attached to or in the medical device in an interchangeable manner.

The documents DE 693 09 757, DE 693 21 264, DE 696 15 507, DE 696 15 633, DE 697 09 192, U.S. Pat. Nos. 5,163,900, 5,282,787, 5,582,601, 5,800,396, 5,897,524, 5,899,674, WO 1987/001943, WO 2004/108189, or WO 2004/110524 show cassettes with similar properties.

In order to attain the aspiration effect, different pump systems are used for the aspirated liquid. In particular, systems with peristaltic pumps or systems with suction by a negative air pressure, generated by a Venturi nozzle, are rival systems, wherein surgeons will prefer one system or the other based on the different aspiration characteristics of said systems in different applications or due to the personal preferences of the surgeon. For example, other liquid delivery systems, such as membrane pumps, etc., can also be used for aspiration, for example.

WO 2010/129128 shows an example of a peristaltic pump in a cassette.

Preferably, sensors, actuators, electronics and/or mechanics are accommodated in the medical device and not in the interchangeable cassette. In particular, the cassette only comprises the parts of the sensor system and the actuators that come into contact with potentially contaminated liquid, for example measuring chamber, membrane, pump or suction arrangements, squeezing regions of valves, etc.—that is to say especially passive parts. The active parts of sensors and actuators, especially if they represent a considerable cost factor, are preferably housed in the medical device. A division of this kind is also recommended in the sense of a meaningful reusability and recycling aspects. For example, the cassette can be formed here as an entirely plastic part, which preferably does not contain any electronic and/or metal components—which amongst other things facilitates proper disposal.

Pressure sensors which only have to detect positive pressure can be implemented here relatively easily. For example, a membrane can be provided in the liquid circuit of the cassette, which membrane is configured in such a way that the pressure of the liquid (relative to the external air) can be detected by a force measurement at the membrane. Here, the force can be determined for example in a known manner, in particular by means of strain gauges, piezoelectric sensors, magnetic sensors, etc.

Alternatively, pressure sensors are also known in which a geometric deflection of a resilient membrane (or the like) is dependent on the liquid pressure in the circuit, preferably in a defined and known dependency. In this alternative the geometric position of a membrane can then be evaluated by a sensor. Here, alternatively to the deflection method, a compensation or zero adjustment method can also be applied for the measurement. Generally, however, a more precise pressure detection, which is more stable in the long term, can be provided by a force measurement, in particular with a negligibly small geometric deflection of the membrane, and therefore this principle is used with preference.

In a pressure detection arrangement which is configured to detect positive pressure as well as negative pressure, the force, or rather the deflection, must be detectable in a positive and also negative direction. An advantage of a force measurement lies for example in the fact that, due to the very small deflection of the membrane, no additional elasticity is introduced into the aspiration path. The pressure stability in the eye, in particular when removing an occlusion, is increased significantly. Accordingly, a connection of the pressure measuring membrane of the cassette to the associated pressure measuring sensors in the device must be configured for transmission of positive and negative values, or alternatively what is known as a biasing—that is to say a shifting of the working point (for example by a constant offset)—must be performed. A mechanical design is therefore more complex accordingly. Examples of such known pressure detection arrangements can be found, for example, in EP 1 253 412, U.S. Pat. No. 5,392,653, or U.S. Pat. No. 3,841,157.

For example, document. DE 600 00 608 also presents a pressure measuring system, in which a membrane drawn over a chamber has a ring, in which a plate is received. A force transducer is coupled removably to the membrane by means of this plate. The coupling can be achieved here, similarly to DE 693 16 209, preferably by a ferromagnetic plate and a magnet on the force transducer. Alternatively, the use of a latching arrangement is proposed, which is configured as a fastening on the plate and can be releasably coupled to a socket on the force transducer by means of a clamping arrangement (such as a grub screw). Amongst other things, one disadvantage here is that the cassette must have a metal part for the magnetic coupling. The coupling and release of the magnetic connection by permanent magnets also constitutes a high mechanical load for the membrane, however the alternative with an electromagnet that can be switched off is also not without these disadvantages and in addition requires a permanent flow of current during the entire operating period. Also, there is in neither case an exact reproducibility of the coupling, and therefore different measurement characteristics can occur with each insertion of a cassette. The proposed use of a grub screw is also hardly workable in practice in an operating environment. In addition, the overall volume of the solution presented therein is rather large, and the direction (orthogonally to the measuring membrane) in which the coupling must be performed in the case of the presented solution is also disadvantageous in respect of an implementation in an ophthalmological cassette and for the process of insertion thereof.

It is an object of the present invention to improve an ophthalmological cassette or to provide an improved cassette. One object here is also to improve and to simplify the pressure measuring unit and to provide a unit of this kind in the cassette.

It is in particular an object here to provide a simple, secure and reliable coupling between cassette and device, which also withstands many replacement cycles.

The improvement and simplification of the cassette in respect of its cooperation with the device, in particular at the time of insertion and removal during the replacement process, constitute a further object of the present invention.

A specific object here is to provide a cassette that has a compact design and/or to improve the recycling capability. It is also a specific object to reduce possible sources of error during handling as well as during; the actual use of the ophthalmological cassette.

It is also an object to provide a functionally flexible and versatile cassette or to provide a single device for flexible use of different cassette options each with specific functionalities adapted to the application. Here, the corresponding cassette options should preferably be compatible with one another.

These objects are solved according to the invention by the features of the independent claims and/or by the features of the dependent claims or these solutions are developed further.

The present invention relates to a replacement part for an ophthalmological apparatus. Here, the replacement part can be configured specifically as an interchangeable ophthalmological cassette, which comes into contact with patient liquid, for an ophthalmic surgical device. For example, the device can be intended for phacoemulsification, vitrectomy, diathermy, femto-lasers, capsulotomy, etc.

The replacement part is constructed here with at least one hard region as housing—in particular made of a hard plastic, especially a thermoplastic such as a polypropylene (PP) or polyethylene (PE)—and at least one soft region—in particular made of a soft plastic, such as: a thermoplastic elastomer (TPE), an elastomer, or a silicone. Here, the hard region and the soft region form inner liquid channels of the replacement part. The soft region also forms here functional elements of the replacement part, at least:

a pump arrangement for pumping liquid into the liquid channels, in particular in the form of a peristaltic pump, a valve arrangement for varying a flow cross-section in at least one of the liquid channels, and a pressure detection arrangement for determining a liquid pressure in at least one of the liquid channels.

The replacement part also has an aspiration connection for the connection of at least one of the liquid channels to an ophthalmic surgical instrument, and a waste connection for discharging liquid, in particular aspirated liquid, into a waste container.

The pressure sensor arrangement is configured here with a pressure chamber, which is connected to one of the liquid channels, and a flexible membrane, which peripherally surrounds a coupling element. Here, the membrane can be configured in particular as a soft region, and in particular can be at least approximately circular and can have at least a common central axis with the coupling element.

The coupling element is configured here with a recess, which in particular is peripheral at least in part, in such a way that a fork-shaped arm of a force measuring arrangement can be inserted. This arm is oriented here substantially parallel to the membrane and can be inserted directly into the recess in such a way that it surrounds the coupling element on at least two sides. The recess of the arm preferably surrounds the coupling element over an angular range of more than 180°. Here, by means of the arm, it is possible to detect a force acting on the membrane, which force is exerted in a direction substantially normal to the membrane. A direct coupling is provided here between the force measuring arm, which in particular is formed as a plate, provided with strain gauges, with fork-shaped recess for direct engagement with the coupling element on one side and a fixed connection to the device on the other side. Here, the strain gauges are preferably applied to a point of the arm at which the cross-sectional area of the arm is reduced.

In other words, a replacement part according to the invention has a pressure measuring chamber, which on an outer side, which in particular is substantially planar, has a coupling element which is surrounded peripherally by a flexible membrane. The coupling element is configured here with a in particular at least partially peripheral—recess, which is configured in such a way that a fork-shaped arm of a force measuring arrangement can be engaged preferably positively from at least two sides, wherein the arm is oriented at least approximately parallel to the membrane. Here, the pressure of the liquid disposed in the pressure chamber acting on the membrane causes a force effect acting substantially in a normal direction in relation to the liquid, which force effect is transferred via the coupling element to the fork-shaped arm of the force measuring arrangement engaging the coupling element. Accordingly, the pressure can be determined both as a negative pressure and as a positive pressure in relation to the surrounding atmospheric pressure, since the force effect can be transferred in both a positive and a negative direction.

Here, the pressure chamber can be configured according to the invention as a hard region (or as a region of the hard region) and the membrane and the coupling element can be configured as a soft region (or as a partial region of the soft region).

The membranes and the coupling element can be configured here integrally, especially integrally as part of the soft region.

The soft region (or a partial region of the soft region) can also form—in particular inner—seals of the pressure measuring chamber and of the liquid channels of the replacement part.

In order to provide open-loop control, closed-loop control and/or monitor the processes during a surgical procedure, in addition to the actuators, which actively influence liquid movements, sensors are also necessary in the liquid circuit. In particular, pressure conditions in the liquid circuit are determined here. Especially since air bubbles in a hydraulic system of this kind could falsify the pressure conditions and/or since an introduction of air into the eye must be avoided, at least a monitoring for air bubbles can preferably also be implemented in the ophthalmological system.

The replacement part can additionally have a flange connection for the connection of a container for providing infusion liquid, and an infusion connection for feeding the infusion liquid to the ophthalmic surgical instrument, which connections are connected internally via separate liquid channels. Here, the separate liquid channels can have in particular an infusion valve for controlling an infusion flow. Alternatively or additionally, the separate liquid channels can also have an infusion pump arrangement and/or an infusion pressure sensor.

Here, the hard region can be formed from a hard plastic and the soft region can be formed from a thermoplastic elastomer, which—in particular at least for individual parts of the replacement part—can be configured as a common, integral multi-component injection-molded part.

Here, the hard region can have recesses, by which regions of the soft region, which preferably form the functional elements, are mechanically accessible from outside the replacement part. In particular, these regions can form at least parts of the functional regions of the pressure sensor arrangement, pressure detection arrangement, of the liquid channels of the pump arrangement, especially of squeezing regions of peristaltic pump, of valve arrangements and/or of active or passive ripple compensation arrangements.

The replacement parts in embodiments according to the invention can also have at least one air bubble detector for detecting air in the liquid channels, which work in particular optically, especially via refraction effects. For example, the hard region for this purpose can be formed from optically transparent material, which forms a viewing window, in particular a polished viewing window, for the air bubble detector. Here, specifically, the evaluation electronics of the air bubble detector can be fixedly installed in the device outside the replacement part.

The replacement part in embodiments according to the invention can also be formed with at least one valve arrangement for controlling the flow in one of the liquid channels. Here, specifically, the control electronics and/or mechanics of the valve can be fixedly installed in the device outside the replacement part and act mechanically merely on a soft region of the replacement part.

In embodiments according to the invention the replacement part can also be formed with at least one ripple compensation of the peristaltic effect between fluid connection and pump arrangement. This can be formed in particular actively by means of an actuator or passively by means of an elastic pressure fluctuation balancing region.

In a replacement part according to the invention in particular also the liquid channels and functional elements can be configured and arranged in such a way that in the installed position the flow direction of the liquid runs for example from the aspiration connection to the waste container in the replacement part substantially against the direction of gravity, and therefore any air bubbles are removed.

The replacement part can also have an outer toothing in the hard region, which toothing is configured such that the replacement part can be automatically pulled in by the ophthalmological apparatus and positioned therein.

The invention also relates to a corresponding ophthalmological apparatus, that is to say a device for eye surgery, in particular with which a suction flushing can be performed during the operation and which is configured to receive an embodiment of a replacement part according to the invention. Here, the apparatus has a receiving shaft for the replacement part, which shaft comprises actuators and sensors, which are designed to be able to interact with the functional elements of the replacement part. In particular, the device has an arm of a force measuring arrangement, which enters into an operative connection with a coupling element of a pressure measuring membrane of a cassette according to the invention in the event that the cassette is inserted linearly. This operative connection is in particular almost free from play in an orthogonal direction in relation to the membrane and is produced by means of a fork-shaped end of the arm, which engages in the coupling element at least on two sides as the cassette is inserted.

The invention also relates to a corresponding method for coupling a replacement part to an ophthalmological apparatus, in which in particular there is a coupling of a pressure measuring sensor, in which a fork-shaped protrusion of an arm of a force measuring arrangement is inserted into an at least partially peripheral recess in a coupling element fixedly connected to a membrane in the liquid channel. The fork-shaped protrusion is preferably inserted linearly in an insertion direction of the cassette into the device.

Part of the invention is also a corresponding method for measuring aspiration pressure with an ophthalmological cassette in an ophthalmological device, with a cassette-side pressure measuring membrane, which has a coupling element, in which a fork-shaped arm of a device-side force measuring arrangement engages in a manner surrounding the coupling element at least on two sides, wherein the pressure measuring membrane and the arm are oriented substantially parallel to one another.

Here, the fork engages from at least two sides with the recess of the coupling element, wherein the fork is then connected the membrane via the coupling element almost without play in a direction normal to the membrane. At the time of pressure measurement, a value of the force effect in the direction normal to the membrane is detected, wherein the geometric deflection of the membrane and the fork remains negligibly small. The releasable connection of the coupling element and fork produced as the cassette is inserted is preferably almost free from play here—especially in a direction normal to the membrane surface—that is to say it has play for example in the order of several hundredths or tenths of a millimeter. A small play of this kind means that the coupling can be performed securely and with low expenditure of force, since the prongs of the fork slide into the lateral recesses of the coupling element and no significant deformations of coupling element and/or membrane occur, and, in particular after the coupling, only negligibly small forces occur in the direction parallel to the membrane. A completely play-free coupling is also not absolutely necessary in accordance with the invention, since it is not a geometric deflection that is determined, but instead a force effect, on which any geometric play has only negligibly small effects. Accordingly, it is also not absolutely necessary for the coupling element to be made rigid in the direction of the force to be measured, and instead the coupling elements may certainly have a certain flexibility, since this likewise has only a usually negligibly small effect on the force value to be determined. The force exerted by the pressure of the liquid onto the membrane and via the coupling element onto the arm is a measure here for the liquid pressure, in particular a positive force for a positive pressure in relation to the atmosphere and a negative force for a negative pressure in relation to the atmosphere.

In other words, in accordance with the invention, in the event that the replacement cassette is inserted linearly into the device, a fork of the device-side arm of the force measuring arrangement can be inserted in a direction lying substantially parallel to the insertion direction and substantially parallel to the membrane of the cassette-side pressure detection arrangement, at least on two sides or also three sides, into the recess of the coupling element of the membrane formed for this purpose and likewise lying substantially parallel to the insertion direction, wherein the fork is inserted in the insertion direction without force or at least substantially without force. Thus, a force-free coupling of device-side and cassette-side parts of the pressure detection arrangement can be implemented, in particular by simply inserting the replacement cassette into the device linearly.

An advantageous method for producing an ophthalmological cassette according to the invention also has mechanically flexible functional elements on at least two opposite sides. The method includes a multi-component injection molding of a hard plastic, forming a hard region, and of a soft plastic, forming at least one functional element. In so doing, a first and a second, opposite, side shell of the cassette are formed. A non-releasable snap fit or press fit of the first and second opposite side shells is then created during the production, wherein the soft plastic forms seals of liquid channels inside the cassette. In a further embodiment a core part, in particular made of hard plastic, can be inserted before the snap fit is established between first and second side shell.

Some of the methods described here are preferably provided at least partially as programmed sequences. The invention therefore also relates to computer program products with program code, which is stored on a machine-readable carrier or which is provided as a computer-data signal, embodied by an electromagnetic wave (for example as a radio signal), for carrying out the method above. Here, the program code can specifically carry out an automatic execution of open-loop and/or closed-loop control tasks described here, and an execution of process sequences in an ophthalmological device, or can be designed for this purpose.

The method according to the invention and the device according to the invention will be described in greater detail below purely by way of example on the basis of specific exemplary embodiments schematically depicted in the drawings, wherein further advantages of the invention will also be discussed, wherein specifically:

FIG. 3a and FIG. 3b show a first embodiment of an example of a replacement part according to the invention in the form of an interchangeable cassette for an ophthalmological device in 3D views from the left and right;

FIG. 3c shows a sectional depiction of the first embodiment of a replacement part according to the invention;

FIG. 3d shows an exploded depiction of the first embodiment of a replacement part according to the invention;

FIG. 4a, FIG. 4b and FIG. 4c show a depiction of an exemplary embodiment according to the invention of a replacement part, which is inserted in a corresponding example of an ophthalmological device according to the invention;

FIG. 5, FIG. 6a, FIG. 6b, FIG. 6c, FIG. 6d, FIG. 6e and FIG. 6f show embodiments of examples of a replacement part according to the invention with focus on the coupling of the pressure detection arrangement according to the invention;

Figure 1:
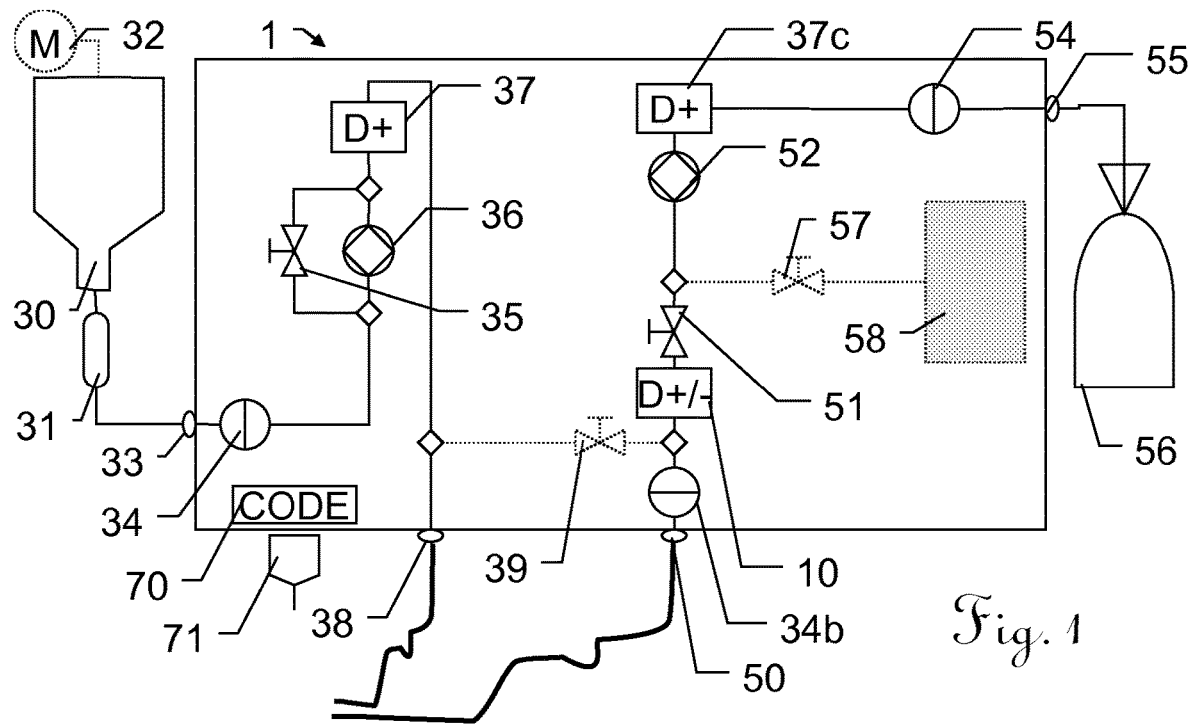
FIG. 1 shows a block diagram of a first embodiment of a replacement part according to the invention for an ophthalmological device.

FIG. 7a, Fi 7b, FIG. 7c and FIG. 7d show embodiments of an example of a replacement part according to the invention with focus on the coupling of the cassette-side pressure detection arrangement according to the invention;

FIG. 8a, FIG. 8b, FIG. 8c and FIG. 8d show a depiction of an exemplary embodiment according to the invention of a replacement part with pressure detection arrangement according to the invention and pump arrangement according to the invention, and cooperation thereof;

FIG. 9a and FIG. 9b show embodiments of an example of a replacement part according to the invention with focus on a cassette-side valve according to the invention;

FIG. 10 shows an embodiment of an example of a replacement part according to the invention with focus on a cassette-side positive pressure sensor according to the invention;

FIG. 11 shows an embodiment of an example of a replacement part according to the invention with focus on a cassette-side air bubble sensor according to the invention.

The depictions in the figures are for illustration purposes only and, unless explicitly stated otherwise, are not to be regarded as true to scale. Identical or functionally similar features shall, as far as practicable, be consistently marked with the same reference numerals and, where appropriate, distinguished by a letter as an index. The presented diagrams show the basic technical structure, which can be supplemented or modified by a person skilled in the art according to general principles.

FIG. 1 shows a possible example of a block diagram of an embodiment of an ophthalmological cassette 1 according to the invention with at least one pressure detection arrangement 10 according to the invention. In this example, it can be specifically a pressure detection arrangement 10 in an interchangeable cassette 1 of an ophthalmological device 99, with which suction flushing can be carried out. In the left half of the figure an active infusion arrangement is shown, and in the right half an aspiration arrangement. A container 30, i.e. for example an infusion bottle or an infusion bag, provides an infusion liquid. This infusion liquid supply can be equipped, for example, with an arrangement for checking the filling level. For example, the container 30 and/or a drip chamber 31 can be monitored for emptying by means of a sensor, and a corresponding warning can be output in good time. As known from the prior art, the infusion liquid pressure at the bottle connection 33 of the cassette 1 (or in the entire infusion system) can be changed or controlled by varying the height of the container suspension by means of a height adjustment of the suspension of container 30, preferably motorized and automatically, this being symbolized here by the drive 32. Here, the connection 33—in the inserted state of the cassette 1 accessible from outside—can be arranged on the cassette 1, and for example can be connected via a tube to the infusion container 30, or to the drip chamber arranged in-between.

The cassette 1 according to the invention can have at least one air bubble sensor 34 in the infusion system, by means of which a correct function can be monitored, and an infusion of air can be avoided. The air bubble detector 34 can work here in particular optically—for example on the basis of different light refraction properties of air and liquid—and also on the basis of other principles, by means of which a distinction can be made between a presence of gas or liquid in the infusion system. An example of a specific embodiment is described further below.

In one embodiment the cassette 1 according to the invention can implement the previously described adjustment or control of the infusion pressure by varying the height difference between the container 30 and the height of the infusion point. Here, the cassette 1 according to the invention can have in one embodiment an infusion valve 35, by means of which the flow cross-section of a liquid channel of the infusion system is variable, in particular can be opened or closed, but optionally also can assume an adjustable intermediate position. An example of a specific embodiment is also described here further below.

In another embodiment of a cassette 1 according to the invention, an active infusion can also be provided by means of an active liquid delivery arrangement 36. To this end, for example a pump arrangement, such as a peristaltic pump or another delivery arrangement for liquid, can be provided in the infusion system. In an embodiment of this kind, an infusion valve 35 and/or a height adjustment of the infusion container 30 can also be omitted, optionally. Here, by appropriate actuation of the delivery arrangement 36, the infusion pressure and/or the delivery volume of the infusion can be varied, in particular controlled by open-loop or closed-loop control.

A further preferred embodiment of a cassette 1 according to the invention can also comprise—as shown in the drawing—an infusion container height adjuster 32 and an infusion liquid delivery arrangement 36. Here, in particular a valve 35 can be configured as a bypass to the delivery arrangement 36. Either an active (i.e. initiated actively by the delivery arrangement 36) or a hydrostatic (i.e. brought about by a difference in height) infusion pressure variation can thus be provided with the same cassette 1. In particular, it is possible to switch here seamlessly between these two principles—i.e. for example also during operation—as necessary, for example in accordance with current requirements of the performed surgical procedure in accordance with the preferences of the surgeon.

The infusion system according to the invention may additionally comprise an infusion pressure measuring arrangement 37, by means of which a pressure in the infusion system can be determined, can be monitored and/or can be controlled. This infusion pressure measuring arrangement 37 is preferably arranged after the infusion valve 35 and/or the pump arrangement 36, and therefore the pressure determined thereby corresponds to the pressure supplied to the eye. Since only positive pressure in relation to the atmosphere can (or at least should) prevail in the infusion system, this infusion pressure measuring arrangement 37 can be configured in such a way that only positive pressure can be determined thereby, and not necessarily also negative pressure. An example of a specific embodiment will also be described here further below.

The infusion liquid is provided by means of the cassette 1 according to the invention with adjustable pressure and/or delivery volume at an external infusion connection 38 of the cassette 1, which can be connected to a line or a tube to the surgical intervention tool, so that the infusion into the eye can be provided with adjustable and/or controllable pressure and/or volume. In order to ensure safety, the actual prevailing pressure of the infusion towards the patient can be monitored by means of an appropriate pressure sensor.

Here, the liquid path in the cassette 1 in the inserted state in the flow direction can preferably be configured in accordance with the invention so as to run substantially from bottom to top, so that a good filling of the aspiration system is achieved, and an accumulation of air bubbles is avoided.

Also shown here is an optional path according to the invention from the infusion system to the aspiration system of cassette, which can be released with a venting valve 39. This can be used, for example, to fill the aspiration system with liquid, especially when the cassette 1 is put into operation, and/or to backflush infusion liquid through the aspiration system, for example to remove occlusions, for a reflux function, or generally to reduce the negative pressure in the aspiration path, for example if the physician wishes to reduce the desired pressure via the foot switch. For these functionalities, further valves may be available in the cassette for the corresponding switching of the liquid flows. Some examples are shown by way of example in the following figures.

The aspiration system of the cassette 1 according to the invention is likewise connected to the surgical intervention tool by a line or tube via an aspiration connection 50. Again, at least one air bubble sensor 34$h$ can be present in the aspiration system, as described elsewhere. The figure also shows an aspiration valve 51, which in particular can be configured in accordance with the general descriptions of valves detailed here.

In the aspiration system, a pressure measurement is also carried out with a pressure measuring arrangement 10. During the aspiration, however, there is the requirement that negative pressures in relation to the atmosphere must be detectable by the pressure measuring arrangement 10, and preferably both negative and positive pressures should be detectable.

In order to attain the aspiration effect, the figure shows two variants: on the one hand a peristaltic aspiration and on the other hand a Venturi aspiration. An embodiment according to the invention of a cassette 1 can have either only the peristaltic aspiration, or another embodiment according to the invention of a cassette 1 can have only the Venturi aspiration, or a further embodiment according to the invention can have both the peristaltic aspiration and the Venturi aspiration.

In the case of the Venturi aspiration the aspiration effect is brought about by negative air pressure which is usually generated by a name-giving Venturi nozzle. However, other negative pressure-generating principles can also be used, in particular such as those in the embodiments of the parallel patent application EP 16197018 filed on the same day by the same applicant and hereby included by reference. These variants are symbolized here by the Venturi valve 57 and the negative pressure system 58.

In peristaltic aspiration, a liquid delivery arrangement 52 is used to generate the aspiration effect. The delivery arrangement 52 can be in particular a peristaltic pump, but optionally a membrane pump or similar liquid delivery arrangements can also be used.

The aspirated liquid is preferably pumped into an appropriate waste container 56, which is preferably connected to an appropriate waste connection 55 outside the cassette 1. Again, a pressure sensor 37c, especially for positive pressure, can be used to detect a pressure increase with a full waste bag.

Alternatively, a differently designed filling level monitoring of the waste container 56 can also be provided. As shown here, a further air bubble sensor 54 can optionally also be provided in the liquid channel to the waste container 56. For example, also in the event of malfunctions, soiling or if the valve 51 is not completely tight during the emptying of the bag, this can be detected by the pressure sensor 10 on the patient side, and appropriate safety measures can be initiated.

The cassette 1, in accordance with the invention, may also have a coding 70, in particular mechanical and/or optical, which can be recorded and evaluated by a corresponding reading unit 71 of the device 99. This coding can be used to prevent multiple or non-sterile use, for example in the case of disposable cassettes, and a specific embodiment of the inserted cassette and its optional functionalities etc. can be detected by the device 99. For example, in one embodiment it can be a printed, engraved or laser-inscribed code 70, especially in the form of a barcode or a QR code 70, which is detected by an optical detection unit 71, such as a camera 71 in the device 99 during or after the insertion of the cassette 1.

Figure 2:
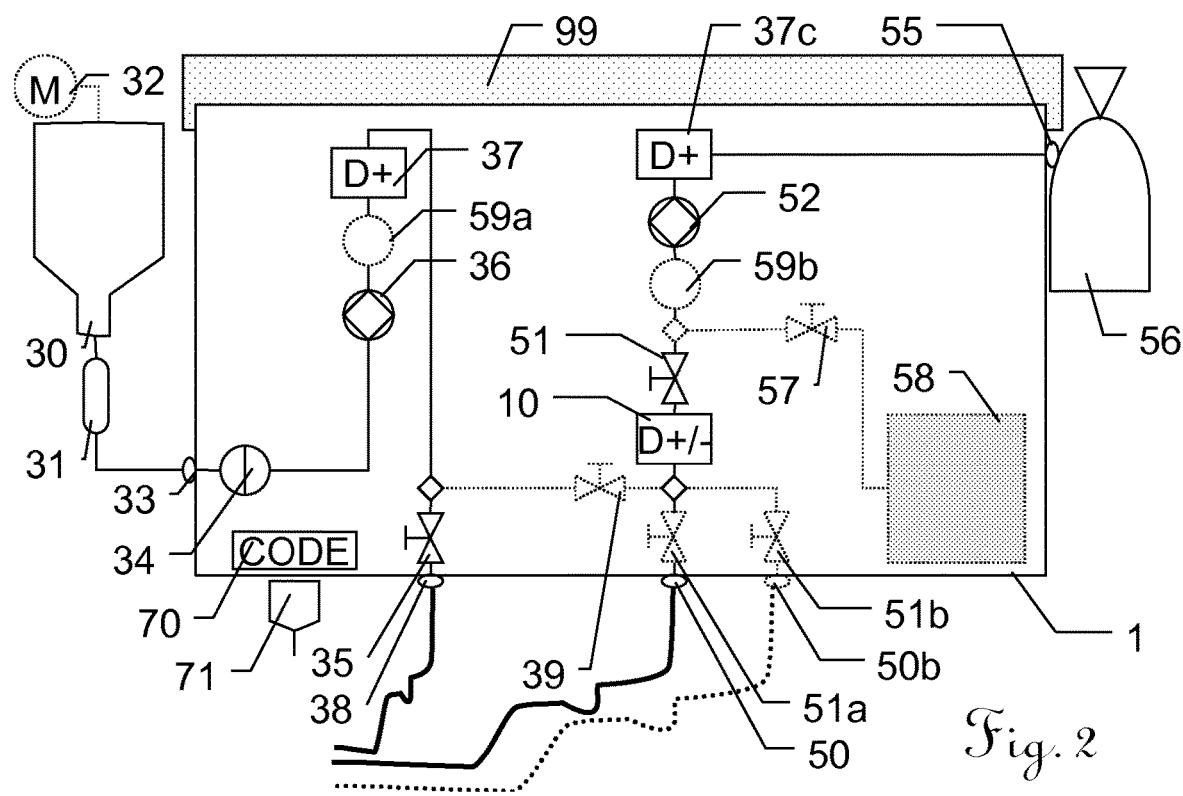
FIG. 2 shows a block diagram of a second embodiment of a replacement part according to the invention for an ophthalmological device.

FIG. 2 shows another exemplary embodiment of a cassette 1 according to the invention in a block diagram. The features functionally identical or equivalent to FIG. 1 are provided with similar reference numerals, and reference is made to their description above.

The main differences between this embodiment according to the invention and FIG. 1 are, according to the invention, that in the infusion area only one active infusion is carried out by means of a delivery arrangement 36. The infusion valve 35 is here optional and can be designed for example as a shut-off against the patient in order to realize additional safety functions or to cooperate with the optional valve 39. In the aspiration area, the waste bag 56 can be attached directly to the cassette 1 in accordance with the invention; a second, optional aspiration connection 50b with corresponding second aspiration valve 51b is shown. Optionally, active or passive ripple compensators 59b and/or 59b for balancing pressure or delivery volume ripples of the peristaltic pump 52 or 36 are arranged for example between the patient and pump arrangement 52 or 36. Various aspects from FIG. 1 and FIG. 2 can also be swapped and/or combined in accordance with the invention for different embodiments according to the invention.

FIG. 3a and FIG. 3b show a further embodiment of a cassette 1 according to the invention, each in a view from the right front (FIG. 3a) and left front (FIG. 3b). In this example, the cassette 1 is shown as a basic cassette 1a, at least approximately cuboid in shape in its outer contours, with a projecting plate as the front section 1b. A shaping of this kind enables a space-efficient stowing and stackability of the cassette 1, in particular for storage, shipment, etc. The shown front section 1b, which forms a handle 1c, enables good handling at the time of insertion into the device 99, in particular while maintaining the stability of the relevant parts of the cassette 1 and above all preventing contamination between the device 99 and the staff in the sterile area. In this embodiment connections for tube systems are also found on the front section 1b, in particular those to the surgical handpiece, to the infusion liquid reservoir 30, to a waste bag 56, etc. Preferably these connections 33, 38, 50, 50, 50b, 55 are mechanically and/or geometrically coded in order to exclude the danger of incorrect connection and confusion. This coding, besides optical marking, can also be provided by different geometrical shaping of the shell 41, 42 and/or of the core part of the cassette 1, by which these connections are formed. The front section 1b of the cassette 1 according to the invention, which front section is externally accessible during the insertion and/or operation, can thus be configured in accordance with one aspect of the invention in such a way that it forms a handle 1c, which enables manipulation of the cassette 1, without at the same time coming into contact with the unsterile device. The front section 1b can also be used as a position stop acting in the direction of insertion as the cassette 1 is inserted into the device 99.

The optional air bubble detectors 34, 34b and 54 can also be seen in this figure. They work optically in the embodiment shown here. For example, they can be configured based on the principle of different refraction indices of liquid and air, in particular a different angle of total reflection between liquid and air, or different light-guiding properties of liquid and air, or another mode of action can be used, for example a capacitive mode of action. These air bubble detectors 34 are preferably located at least approximately in the vicinity of the associated connections 33, 38, 50, 50b and/or 55. For example, an air bubble detector 34, 54 of this kind can be configured with a viewing window in the liquid channel, which viewing window is optically transparent at least in the used wavelength and is provided in an outer shell 41 and/or 42. In one embodiment the outer shell can be formed for example of transparent material. FIG. 11 illustrates an exemplary embodiment according to the invention.

In accordance with a partial aspect of the invention, the arrangement and design of the liquid channels within the cassette 1 is preferably such that, as the liquid channels are filled with liquid, they always fill (at least substantially) from bottom to top—whereby any air bubbles (corresponding to the medium density ratio) are displaced upwardly and are removed away from the patient. A filling of this kind of the liquid channels of the cassette is realized here in particular following the insertion of the cassette 1 when the cassette 1 is put into operation. Accordingly, in accordance with this aspect of the invention, the arrangement of the connections from bottom to top can be provided in the following order: waste bag 55—aspiration A from the patient 50—possible aspiration B 50b-infusion to the patient 38—infusion bottle 33.

In the shown example of FIG. 3c the cassette 1 shown in section is constructed substantially in three parts, with a left outer shell 41, a right outer shell 42, and a core part 43. Outer shells 41 and 42 preferably can be snapped, pressed or squeezed against one another and/or against the core part 43, that is to say for example can be embodied with a hook system, a press-fit system, or the like, which in particular might not be releasable again. Press-fit connections 25 are shown in the figure by way of example. In another embodiment the cassette 1 according to the invention can also be constructed only in two parts, i.e. in particular without separate core part 43, wherein the liquid channels within the cassette can be formed by the two outer shells 41 and 42.

In addition, part of the functional elements is shown in this sectional illustration. Here, the soft plastic component of the two-component injection-molded outer shells 41 and 42 is engaged under tension and/or form fit, so that the liquid channels or lines within the cassette are formed. In the shown section the soft plastic forms beads along the liquid channels, which beads in the assembled state engage in the indentation of the core part 43, whereby a liquid seal is provided, in particular by squeezing of the soft plastic and/or forming of a meandering seal with at least a single gradation. Partial regions of the soft plastic component are accessible here from outside in the assembled state of the cassette 1 and form the functional elements. The hard plastic component of the two-component injection-molded outer shells 41 and 42 has corresponding cut-outs for this purpose.

In the embodiment shown here the outer shells 41 and 42 are formed as integral two-component injection-molded parts from a hard plastic and a soft plastic 44. For example they are formed with a polyethylene, polyamide or polypropylene, or another rigid plastic, suitable and permitted for medical applications of this kind, as hard plastic, and for example with a silicone or an elastomer, in particular thermoplastic elastomer, or another soft plastic 44, suitable and permitted for medical applications of this kind. The core part 43 is likewise formed from a hard plastic, for example one of the aforementioned hard plastics. Optional sterilizability of the entire cassette, for example in an autoclave, etc., can also be taken into account when selecting the cassette materials if a reusable embodiment is desired.

FIG. 3d shows an exploded depiction of an exemplary cassette 1 according to the invention, wherein, for the sake of completeness, the soft plastic regions 44a and 44b are also shown separated from the respective associated hard plastic parts 41 and 42, although these can be manufactured integrally as two-component injection-molded parts. In the shown example the soft plastic portions of the outer shells 41 and 42 of the two-component injection-molded parts consist of a thermoplastic elastomer (TPE) and are formed in such a way that they together with the core part 43 form the liquid channels within the cassette 1 and the functional elements (such as pump portions, valves, pressure sensors). In particular, an embodiment with two-component injection-molded outer shells 41 and 42 made of hard plastic can be formed with soft plastic, and a one-component core part 43 can be formed from only hard plastic. If, in an embodiment of this kind, only regions of the core part and regions of the soft plastic come into contact with the patient indirectly via the liquids, but not parts of the outer shells 41 and 42, any medical material guidelines must also be observed only in respect of the core part and soft plastic materials, whereas the material selection for the outer shells 41 and 42 is more flexible in this respect, and for example can be selected primarily in a manner suitable for the strength and aesthetic requirements.

In the examples of embodiments shown in FIG. 3a, FIG. 3b, FIG. 3c and FIG. 3d, the functional elements are each divided over both of the shown outer shell halves 41 and 42, thus enabling a compact structure to be attained. Here, in the shown example, in particular the squeeze pump portions are arranged on one cassette side 42, and the valves and pressure sensors are arranged on the other cassette side 41. Such a division of the functional elements is not mandatory, but can be advantageous with regard to gripping or clamping the cassette 1 in the device 99, in which clamping, fixing and/or fine positioning of the cassette 1 in the device 99 can take place simultaneously with the pressing of the roller head(s) of the peristaltic pump. FIG. 4b and FIG. 4c illustrate an exemplary embodiment of a peristaltic pump according to the invention of a cassette 1 according to the invention. Here, the movement necessary to clamp the cassette in the device 99 is performed only from one side, preferably from the side of the peristaltic rollers 73. For example, slanted faces can be formed here, for example in the region of the center of rotation 75 of the peristaltic rollers or also elsewhere on the cassette 1 and/or on the clamping arrangement of the device 99, which, following insertion of the cassette 1 with appropriate device-side counterparts, bring about a positioning and fixing of the cassette 1 within the device 99.

FIG. 4a schematically shows such a clamping and fixing of the inserted cassette 1 in the device 99 in a side elevation view, with viewing direction towards peristaltic pumps of the cassette 1. Here, a roller head 72 on the device side 99 with rollers 73 is shown, which rollers 73 roll on the squeezing region of the outer shell 42, which squeezing region is bulged in a bead-like manner and is formed of soft plastic 44b. With this rolling, the squeezing region is pressed by the rollers 73 sealingly onto the core part and, with a rotation of the roller head 72 and the center of rotation 75, a volume in the squeezing region 94 between the rollers 73 is conveyed.

FIG. 4b shows the cassette 1 inserted in the insertion direction 91, which runs orthogonally to the drawing plane, into the device 99 up to its end position, but not yet clamped. This is a sectional view through the right and left centers of rotation 75 of the two separate peristaltic pumps 36 and 52 shown here. In this example of an embodiment according to the invention, the cassette 1 is clamped after insertion and, at the same time, the roller heads 72 of the peristaltic pump are pressed in direction 83. As shown, the clamping force of the rollers 73 and/or the position alignment 82 can be determined by means of springs.

Actuators, which are not visible here and which act on the valves 35, 39, 51, 51b and/or 57 are also arranged in device 99 in accordance with the invention. They can be designed, for example, as electromagnetically or electromotively or pneumatically actuated movable tappets in the device which act mechanically on the valve shapings of the cassette 1. A flow cross-section of a portion of the liquid channels can be varied here in the cassette 1, in particular released or blocked. FIGS. 9a and 9b illustrate an exemplary embodiment.

A pressure detection arrangement 10 according to the invention, especially its coupling element 49, is also shown on the cassette 1 and in the inserted state of the cassette 1 cooperates with the device-side force sensor 11, which is not shown here. In the shown embodiment the coupling element 49 of the force sensor protrudes beyond the outer shell 41 and when inserted, for example along a device-side groove in the insertion direction, can be introduced until coupled with the force sensor 11. In a pressure detection arrangement 10 according to the invention, which must have the function of determining both positive pressure and negative pressure in relation to atmospheric pressure, a negative force—that is to say directed inwardly in relation to the cassette sleeve—on the membrane is to be detected. Thus, the simple application of a membrane against a sensitivity surface of a force sensor, as described previously in the case of a sensor that is purely a positive pressure sensor 37, is insufficient since in this case only forces acting outwardly in relation to the cassette sleeve can be detected.

A pressure detection arrangement 10 according to the invention in a cassette 1, particularly if this comprises two-component injection-molded parts, has a multitude of advantages compared to the prior art, for example a less complex design with fewer parts, a simplification of the production process of the cassette, fewer production machines which have to be operated under sterile conditions, no, or less complex checks on weld seams or adhesive seams, lower assembly efforts in respect of the cassette manufacture, simplified handling of the cassette 1 at the time of insertion, reliable coupling of the pressure detection arrangement 10, automatic coupling of the pressure detection arrangement 10 by simply inserting the cassette 1 linearly, possibility for mounting of optional auxiliary modules on the cassette or diversity of cassette variants since all manipulations of the functional elements of the cassette 1 are performed from the side and the cassette can vary in respect of its length in the insertion direction, advantageous packing format for compact storage of the cassette 1, and many more.

FIG. 4c shows the cassette 1 in the clamped state in the device, in which all sensors and actuators of the device 99 correspond with their counterparts of the cassette 1 for interaction therewith. In the shown example this is achieved by a clamping of the cassette 1 in the device 99, which is implemented by the roller heads 72 pressing against the cassette in the direction 83, whereby the cassette 1 is inserted to the left in the drawing plane against corresponding mechanical stops. In so doing, the rollers 73 squeeze the squeezing channels 94—wherein in the upper pump (for example the infusion pump 36) a section through the roller 73 shows a squeezed squeeze cross-section 94 and in the lower pump (for example the aspiration pump 52) there a section next to a roller 73 shows, correspondingly, an unsqueezed squeeze cross-section 94. With the centering elements 82, which in this example also form the rotation axis 75 of the roller head 72, fine positioning of the cassette 1 in the device 99 is also achieved when the cassette 1 is clamped.

FIG. 5 now illustrates a detail of an exemplary embodiment of a cassette 1 according to the invention which is inserted in the device 99. Here, the fork 11 of the device-side force sensor according to the invention is engaged with the cassette-side coupling element 49, according to the invention, of the pressure detection arrangement 10. Both positive 92a and negative 92b force effects 92 exerted onto the membrane 48 by the pressure conditions in the cassette 1 are thus transmittable. The force effect 92 is here at least approximately normal to the surface of the membrane 48 and also at least approximately normal to the insertion direction 91. Here, the shown arm formed by the fork 11 comprises at least part of the measurement electronics 14, in particular a first amplifier stage, by means of which the force effect 92 for detection is provided as an electrical signal. In this embodiment a force measurement by means of strain gauges is shown, these being arranged at a point of the arm which has a reduced cross-sectional area. At least one first electronic amplifier and/or evaluation stage is also arranged directly on or at the arm, particularly in order to avoid electrical interfering influences. The rear portion 17 of the arm is anchored fixedly in the device 99.

The production according to the invention of the connection to the cassette-side pressure detection arrangement 10 can be realized in the shown embodiment in the insertion direction 91 of the cassette 1 into the device 99, in that, as the cassette 1 is inserted into the device 99, the fork 11 of the device-side pressure detection arrangement 10 is brought into engagement with the nipple-shaped coupling element 49 of the cassette-side pressure detection arrangement 10. In so doing, the fork 11 engages in the recess 46 of the coupling element 49, which recess 46 could also be referred to as a slot 46 or notch 46. The fork is oriented here substantially parallel to the membrane 48, and the fork 11 surrounds the coupling element 49 at the position of the recess 46 at least in part—preferably at least on two opposite sides of the coupling element 49 in the recess 46. Here, the fork and/or recess 46 can preferably also be designed with a chamfer, in particular in order to be able to withstand greater tolerances relative to one another of the regions engaging with one another during the insertion process, so that the cassette 1 does not have to be guided so precisely around the device 99.

FIG. 6a shows an example of embodiment according to the invention in which the cassette 1 is inserted only partially into the device 99. The insertion direction here constitutes the movement of the cassette 1 relative to the force sensor 11, which is fixed in the device 99. Here, the fork of the force sensor 11 is at the front, flat tongue of the arm of the force sensor, just before engagement in the cassette-side pressure detection arrangement 10—the cassette 1 is thus inserted almost fully. The prongs of the fork 11 are about to engage in the insertion direction in the recess 46 of the coupling element 49. The membrane surface 48 of the pressure chamber 47 of the cassette 1 is arranged here parallel to the insertion direction (at least approximately—that is to say marginal deviations due to tolerance or play are possible). The fork 11 of the device-side arm are arranged (at least approximately) parallel to the insertion direction 91 and thus also (at least approximately) parallel to the membrane 48. In accordance with the invention, the recess 46 and the coupling element 49, in which the fork 11 engages with the coupling element 49 at least on two sides, is accordingly formed substantially parallel to the insertion direction 91 of the cassette 1.

FIG. 6b shows an example of an embodiment according to the invention in which the cassette 1 is fully inserted—the cassette 1 is thus in the end position provided for operation thereof. Here, the fork 11 of the device-side force sensor 14 is engaged in accordance with the invention with the coupling element 49 of the cassette-side pressure detection arrangement 10, and a measurement according to the invention of positive pressure and negative pressure can be performed. In the shown example, with inserted cassette 1 at the coupling element 1, the prongs of the fork 11 are engaged not only laterally, but the rear part of the fork-shaped, flat arm 11 situated between the prongs is also engaged with the recess 46 of the coupling element 49—the coupling element 49 of this embodiment according to the invention is thus designed and arranged in such a way that it can be engaged by the fork 11 in the coupling element 49 over an angular range of more than 180°, which can be advantageous in respect of the force transmission to be implemented from the membrane 48 to the force sensor, in particular since this brings about a reliable coupling.

FIG. 6c and FIG. 6d show an exemplary embodiment of a coupling element 49 according to the invention of a pressure detection arrangement 10 in a sectional view. A three-dimensional view is shown on the left in FIG. 6c, in which an outer shell 41 of the cassette 1 has been produced from hard plastic with a soft plastic 44a as two-component injection-molded part. The soft plastic 44a forms functional elements, especially the pressure detection arrangement 10 shown here, and seals 93 of the liquid channels 47 inside the cassette. A valve 51 can be seen in the background and is likewise formed in part from the soft plastic 44a. These liquid channels 98 are formed by the outer shell and the core part 43, which is likewise made of hard plastic. In the shown section a region of one of the liquid channels 98 forms a pressure chamber 47 of the pressure detection arrangement 10. This pressure chamber 47 is connected to one of the liquid channels 98 or is traversed by one of the liquid channels 98—which here for example is shown by the inlet in the rear region of the pressure chamber 47. The pressure chamber 47 shown by way of example has a base made of the hard plastic of the core part 43, which by the soft plastic 44a of the outer shell 41 is sealed around the soft plastic 44a-apart from a connection to the liquid channels 98—in that the soft plastic 44a forms a seal 93.

The soft plastic 44a likewise forms the upper cover of the pressure measuring chamber 47, which is formed at least in part as a flexible membrane 48. The coupling element 49 protrudes outwardly from the membrane 48 (in relation to the pressure chamber 47). In this example the coupling element 49 is likewise formed from the soft plastic 44a, but due to its solid design has only a minor elasticity—in particular a much lower elasticity than the membrane 48. The membrane 48 surrounds the coupling element 49 peripherally. The coupling element 49 is thus preferably arranged at least approximately centrally in the membrane 48, and the coupling element 49 is surrounded by the flexible membrane 48 and is connected thereby integrally, but flexibly to the cassette outer shell 41. During the pressure measurement the pressure prevailing in the pressure chamber 47 now acts on the outer walls of the pressure chamber 47 and therefore also on the inner face of the cover of the pressure chamber 47. The surface area times pressure, as is known, gives a force effect 92 which acts inwardly or outwardly depending on the sign of the pressure in relation to the atmospheric pressure. Since the membrane 48 is flexible, this force effect 92 acts on the coupling element 49. By means of a device-side force sensor 14 coupled to the coupling element 49, a value of the liquid pressure in the positive and negative direction can thus be detected via this force effect 92. The walls of the pressure chamber are formed here as a result of the manufacturing process with a layer of soft plastic 44a above the hard region 41, so that the peripheral seal 93 of the pressure chamber and the membrane 48 are formed integrally—this, however, is not absolutely necessary.

The coupling element 49 is formed here in such a way that as the cassette 1 is inserted into the device 99, a device-side arm of the force sensor 14 automatically engages the coupling element 49, so that the force effect 92 can be transferred from the pressure chamber 47 in a positive and negative direction to the force sensor 14. The engagement is realized here automatically as the cassette 1 is inserted, so that no manual manipulations are necessary for the coupling of coupling element 49 and force sensor 14. In the shown example the cassette 1 is inserted into a slot provided in the device 99 for this purpose—in so doing the coupling element 49 and fork 11 of the force sensor are automatically coupled. Besides the insertion performed entirely manually, the cassette 1 can also be inserted here in an automated manner, at least in part, for example by a cassette 1 inserted into the slot of the device 99 being drawn in motorized. At the time of insertion, the cassette 1 is positioned in an intended operating position in the device 99, so that the position of the functional elements of the cassette 1 matches that of the corresponding sensors and/or actuators of the device in order to perform their function. This positioning can be realized for example using guide rails, mechanical stops, position sensors and/or other arrangements suitable for this purpose.

For coupling to the force transfer 14, the coupling element 49 is formed here with a recess 46, which is formed as at least one, at least partially peripheral recess in the coupling element 49. This recess 46 is designed to engage a fork-shaped arm 11 of the force sensor 11 as the cassette 1 is inserted into the device 99. This engagement is provided at least on two opposite sides of the coupling element 49. The recess 46 can thus be designed for example in the form of two opposite lateral slots, in which two prongs of the fork-shaped arm 11 engage. Alternatively, a single recess 46 can be formed at least partially peripherally, that is to say in particular over more than 180° of the coupling element 49, so that not only the prongs of the fork 11, but also the rear connection between the prongs can engage in the recess 46 of the coupling element 49.

To the right, a sectional illustration of a drawing of an exemplary design detail is shown in FIG. 6d, similarly to the above description, in which some of the previously described details can be better seen.

FIG. 6e and FIG. 6f show a further view of an exemplary embodiment of a cassette-side pressure detection arrangement 10 according to the invention, especially of the coupling element 49 of the pressure detection arrangement 10. A 3D view is again shown in the left image 6e, and a design detail thereof is shown in the right image 6f. The coupling element 49 according to the invention in this example has a recess 46 which extends over three sides of the coupling element 49. In order to improve the stability, a fourth side of the coupling element 49 without recess 46 is provided in this embodiment, since the fork 11 cannot engage on this side—alternatively, however, the recess 46 can also be fully peripheral, especially if the rigidity of the coupling element 49 is still sufficient for this application.

In the shown embodiment the recess 46 has a chamfer 45 which increases the interception range for the arm 11 of the force sensor 14 as it is inserted and thus facilitates the coupling. Additionally or alternatively the prongs of the fork-shaped arm 11 of the force sensor 14 can have a chamfer or bevel at their ends, accordingly, as can be seen for example in FIG. 5 and in FIG. 6a and FIG. 6b. The interception range during the coupling process can thus be further increased, and the coupling as the cassette 1 is inserted can be made more reliable.

FIG. 7a shows an exemplary embodiment of a cassette 1 according to the invention in which the cassette-side pressure detection arrangement 10 according to the invention with the device-side arm of the force sensor 11, and portions of two peristaltic pumps 36 and 52, positive pressure sensors 37c and valves 39 and 51, and a plurality of press-fit connectors 25 are shown by way of example.

The liquid channels 98 in the region of the peristaltic pump 36 or 52 are formed within the cassette 1 by the hard plastic core part 43, via which a soft plastic region 44b of the outer shell 44 bulged towards the outer side of the cassette 1 forms a partial region of the liquid channel 98. This partial region, which is also referred to as the squeezing region 94 of the pump, can be squeezed by engaging, device-side rollers 73 in the manner of a peristaltic pump, whereby, as the rollers 73 move, the liquid or air situated in the liquid channel can be conveyed. See also FIG. 8a to FIG. 8d with regard to the pump arrangement.

A positive pressure sensor 37 and/or 37c designed in accordance with the invention and which in respect of its function must be configured to determine only positive pressures in relation to atmospheric pressure can be configured in the embodiment shown here for example with a membrane surface 37c, accessible in the outer shell 41 of the cassette 1, of a pressure chamber in a liquid channel of the cassette 1, against which membrane surface 37c a sensitivity surface of a force sensor 85 in the device 99 bears flat when the cassette 1 is inserted and clamped. The force exerted by the pressure of the liquid in the cassette 1 onto the membrane is transferred to the sensitivity surface of the force sensor 85 and the device 99 by means of the flexible membrane 37c. The value of this force, which presses positively on the sensitivity surface and which is detected by the force sensor 85, is proportional to the pressure in the liquid channel.

The described force sensor 85 can be embodied as a pressure sensor. FIG. 10 illustrates an exemplary embodiment according to the invention.

FIG. 7b shows a sectional view through a cassette 1 of an exemplary embodiment of the cassette 1 according to the invention which is inserted into a device 99 according to the invention. In particular, exemplary liquid channels 98 and press fit 25 or snap connectors 25, by means of which the cassette 1 is joined together, can be seen in the sectional view of the cassette 1. A force sensor 11b according to the invention is shown in the rear region and is intended for a longer cassette variant, which is not shown here, in the device 99.

Also shown is an embodiment of a cassette-side coding 70a and an associated device-side code evaluation 71a—in this example in the form of switch elements, which are actuated in accordance with a shaping of the cassette 1—for example so as to be able to identify different embodiments of cassettes. Furthermore, an exemplary embodiment of an automatic pull-in for the cassette 1 into the device 99 is also shown—in this example with a cassette-side toothing and a device-side gearwheel, which as the cassette 1 is inserted engages in this toothing and by means of which the cassette can be drawn in automatically into its end position or can be ejected following use.

FIG. 7c shows an exemplary embodiment of a cassette 1 according to the invention prior to insertion into a device 99, of which only part of a cassette shaft is shown. What are shown in particular are the force sensors 11 and 11b in the device, which will cooperate with the pressure sensor 10 of the cassette 1 situated in the rear side (not visible) of the cassette when the cassette is inserted. In order to be able to receive the coupling element 49 protruding beyond the outer sleeve of the cassette 1, a groove is formed in the cassette shaft in the insertion direction towards each force sensor 11, 11a. The insertion is achieved by inserting the cassette 1 into the cassette shaft in the insertion direction 91.

FIG. 7d shows the inserted cassette 1 in its end position in the cassette shaft, in which in accordance with the invention the cassette-side pressure sensor 10 is coupled to the device-side force sensor 11, and the other device-side sensors and actuators in relation to the cassette are in a position in which these can cooperate with their respective counterparts in the cassette 1 as intended.

Figure 8A:
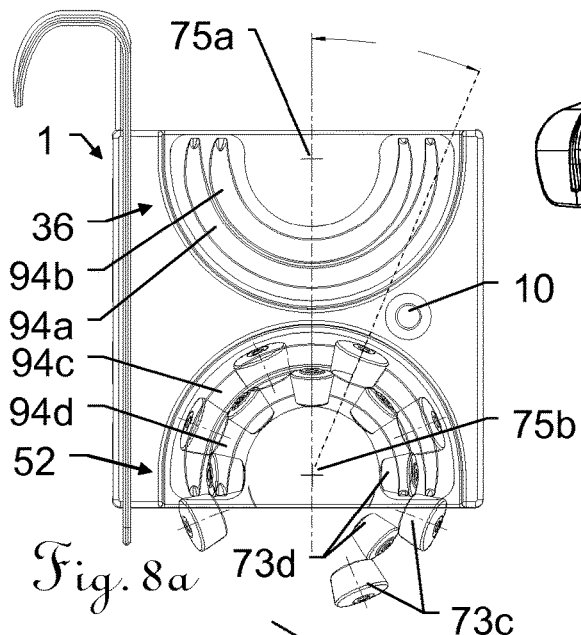

FIG. 8a shows an exemplary embodiment of a cassette 1 according to the invention in which the cassette-side pump arrangement 36, 52 according to the invention in the form of a peristaltic pump is shown. FIG. 8b shows the same, again in a sectional illustration through the cassette 1.

What are shown are a first pump arrangement 36 and a second pump arrangement 52, separate therefrom, for example one for the infusion and one for the aspiration. These are formed with the soft regions 44b of the outer shell 42, which form outwardly bulged squeezing channels 94. By the engagement of rollers 73 (that is to say the shown rollers 73c and/or 73d), these squeezing channels 94a, 94b, 94c, 94d are pressed locally sealingly against the core part 43. By moving the rollers 73, a volume in the squeezing channels 94 can thus be conveyed.

A further partial aspect according to the invention shown here for reducing above-mentioned ripple effects lies in a twofold embodiment with at least two adjacent squeezing regions 94c and 94d. These are designed in such a way that ripples of the adjacent squeezing channels 94c and 94d occurring as a result of the squeezing pumping effect balance out one another completely where possible, and therefore the total ripple is reduced. This can be brought about for example by squeezing rollers 73c and 73d that are offset relative to one another, by means of which a phase shift of the ripple from the two squeezing channels 84c and 94d is brought about. Here, the two inlets and the two outlets of the squeezing channels 94c and 94d are connected to one another in each case. In particular, a phase shift of the ripple courses by approximately 180 degrees in the case of two channels can bring about an advantageous reduction. With a different number of squeezing channels 94, the phase shift must be selected differently accordingly. Alternatively or additionally the position and/or shaping of the inlets and/or outlets of the two squeezing regions 94 can also be formed differently in order to bring about said phase offset and/or a further ripple reduction. A ripple reduction in relation to an individual squeezing region can thus be attained with a corresponding design.

In the case of the at least approximately concentric arrangements, shown here, of two interconnected squeezing channels 94c and 94d, it can additionally be taken into consideration here that different arc lengths also occur with the different arc radii. For ripple compensation, the liquid channel cross-sectional dimensions, cross-sectional shapes and/or cross-sectional courses of the outer arc 94c relative to the inner arc 94d can therefore be formed differently from one another in accordance with the invention in such a way that the volume conveyed per movement unit of the rollers 73 always remains at least approximately the same—or the volumes always balance out one another where possible and together give the smallest possible ripple of the total delivery volume. For example, this is thus achieved in such a way that, over an entire revolution of the roller head supporting the rollers 73, the outer and the inner squeezing path 94c and 94d each convey at least approximately the same volume. Different squeezing radii, caused by different diameters of the engaging rollers 73c and 73d, can also be taken into account in these considerations.

Figure 8C:
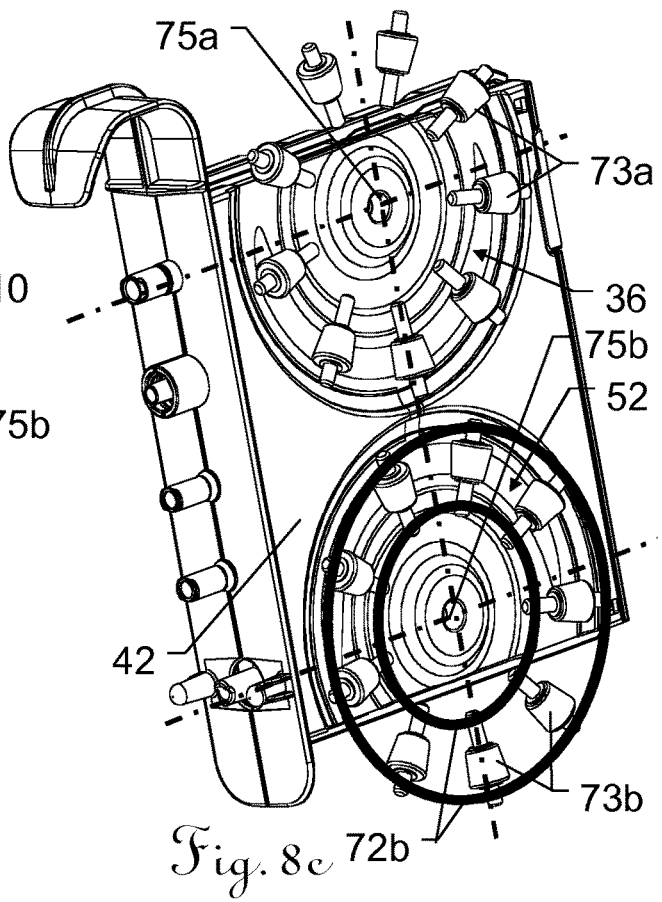
Figure 8B:
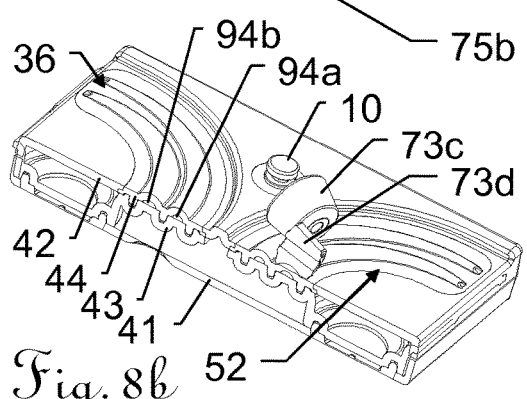

FIG. 8c shows a cassette 1 with engaged exemplary roller heads 72. For the sake of simplicity, only the lower rotatable roller head 72b, on which the rollers 73b are mounted, is shown in the figure—in the case of the upper pump arrangement only the rollers 73a, but not the associated roller head 72a, are shown. In the example shown here a first roller head 72a and a second roller head 72b of the pumps engage on the same side of the cassette 1, but in another embodiment first and second roller head 72a and 72b can also engage on opposite sides of the cassette 1. In particular, but not necessarily, the rotation axes of the roller heads can be arranged here oppositely and can form an at least approximately common rotation axis, which can bring advantages in respect of the force distribution over the cassette 1.

In the example of the embodiment according to the invention shown here, the two pumps 36 and 52 each describe at least approximately a semicircle on the cassette 1. In the case of the cassette 1 shown by way of example, thus results in an advantageous utilization of the space conditions, especially alongside simple handling and producibility. A concentric arrangement of the two pumps 36 and 52, which likewise is feasible, would also be possible but would be comparatively more complex in terms of construction. Alternatively, the bead-shaped squeezing region 94 of the pump 36 and/or 52 can be formed in another embodiment also with another, in particular shorter arc length, wherein however a corresponding arrangement and number of rollers 73a and 73b must always be selected so that a sufficient pump behavior can be ensured and at least one roller 73a is always in engagement in each squeezing region 94.

In order to attain an advantageous rolling behavior, the rollers 73a and 73b are preferably not cylindrical in accordance with the invention, as depicted in the shown example, but instead are configured as truncated cones. The shaping and arrangement are provided here preferably in such a way that the periphery of the rollers 73a and 73b is at each point proportional to the periphery corresponding to the circular path described by the roller at this point around the center of rotation 75a, 75b of the roller head 72b.

In particular, in accordance with the invention, the cross-sectional area of the squeezing region 94 formed here can vary over the length thereof. As shown in this example of an embodiment according to the invention, for example a tapering of the cross-section towards the outlet of the pump 36, 52 and/or an enlargement or reduction of the unsqueezed cross-section of the squeezing region 94 at the inlet of the pump 36, 52 can be provided. Here, in particular with an optimization of this squeezing cross-sectional change, a minimization of pressure and/or delivery volume fluctuations (also referred to as ripples) during the delivery can be attained. An advantageous cross-sectional course along the squeezing region 94 can be attained for example also by means of simulation and/or series of tests.

Figure 8D:
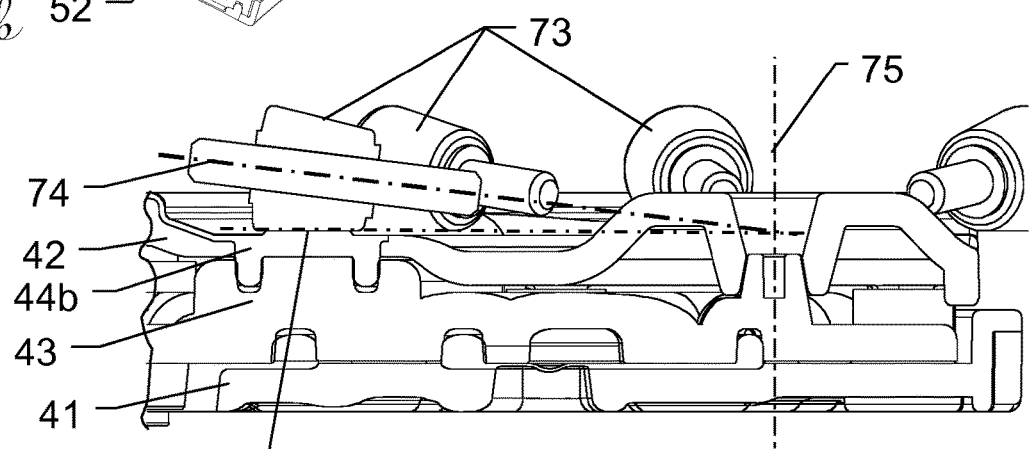

As illustrated in FIG. 8d, this can be obtained for example in accordance with the invention by arranging the roller axes 74 at an incline relative to their rolling planes over the squeezing channels 94, preferably intersecting this rolling plane in the center of rotation 75 of the roller head 72 supporting the rollers 73. The truncated cone-shaped rollers 73 thus roll optimally on the soft plastic region 44b of the outer shell 42 forming the squeezing channels 94, and squeeze these against the core part 43.

Alternatively, however, other geometries can also be used.

FIG. 9a and FIG. 9b show an exemplary embodiment of a valve 35, 39, 51, 51b and/or 57 according to the invention in a cassette 1 according to the invention. Here, the functional region of the cassette 1 forming the valve 35, 39, 51, 51b and/or 57 and embodied with soft plastic 44a is engaged by a tappet 80a or 80b on the device side 99. With a valve according to the invention a partial region of the liquid channel of the cassette 1 is influenced in its cross-section. In particular the cross-sectional region as shown to the left in FIG. 9a by 81a is either released when the tappet 80a is raised, or, as shown on the right in FIG. 9b by 81b, is closed when the tappet 80b is applied, in that a partial region of the soft plastic 44a is pressed by the tappet 80b against the core part 43—and therefore the cross-section of the liquid channel at this point is closed. The moving tappet 80a or 80b is in this case part of the device 99. The valve 35, 39, 51, 51b and/or 57 is situated on the outer shell 41 of the cassette 1, and a region by which the liquid channel 98b can be closed can be formed from the soft plastic 44 of the two-component injection-molded outer shell 41, and this region can cooperate in particular with the core part 43 during the closure.

FIG. 10 shows an exemplary embodiment of a positive pressure sensor 37 and/or 37c according to the invention in a cassette 1 according to the invention. In the shown embodiment a region of the soft plastic 44a of the two-component injection-molded outer shell forms a membrane surface 87, which on its inner side is hydrostatically connected to a liquid channel 98b of the cassette 1, preferably is traversed thereby. Once the cassette 1 has been inserted into the device 99, a device-side force sensor 85 or pressure sensor 85 is brought by means of its sensitivity surface 86 from outside into abutment against the membrane surface 87. The pressure in the liquid channel 98b can be detected on the basis of the force effect thus determinable—exerted by the pressure in the liquid channel 98b onto the membrane surface 87 and via this onto the sensitivity surface 86.

FIG. 11 shows an exemplary embodiment of an air bubble sensor 34 according to the invention in a cassette 1 according to the invention. This works optically in that a light source 95 (for example an LED) emits light into the liquid channel, and a light sensor 96 (for example a photodiode) evaluates received light. In the shown example a light-guiding plastic part 97 is used here on the device side 99 and cooperates with the cassette-side air bubble sensor 34. In a preferred embodiment an air bubble sensor 34 on the cassette side 1 can be formed with an optically transparent hard plastic of the outer shell 41, which forms a window—for example a polished window—towards a region of the liquid channel 98. Alternatively, a transparent insert part or additional transparent component can also be applied in the case of a multi-component injection-molding process.

The invention claimed is:

1. A replacement cassette configured for at least partially inserted into an ophthalmological apparatus in an interchangeable manner, the replacement cassette comprising:
   at least one hard region as housing of the replacement cassette; and
   at least one soft region,
      wherein the at least one hard region and the at least one soft region form inner liquid channels of the replacement cassette, and
      wherein the at least one soft region forms a cassette-side pressure detection arrangement for determining a liquid pressure in at least one of the liquid channels,
   wherein the pressure detection arrangement is formed in the replacement cassette and comprises a flexible membrane and a coupling element,
      the flexible membrane defining an outer wall of a pressure chamber, which is connected to the at least one of the liquid channels,
      the coupling element protruding outwardly with respect to the pressure chamber, and
      the flexible membrane peripherally surrounding the coupling element,
   wherein the coupling element is formed with a recess in such a way that, as the replacement cassette is inserted substantially parallel to the membrane into the ophthalmological apparatus, a fork-shaped arm of a force measuring arrangement of the ophthalmological apparatus engages in the recess substantially parallel to the membrane in such a way that the coupling element is surrounded at least on two sides by the fork-shaped arm and a force effect on the membrane occurring in a direction substantially normal in relation to the membrane is detectable by the force measuring arrangement both in a positive and in a negative direction, and wherein the recess is formed substantially parallel to an insertion direction of the replacement cassette into the ophthalmological apparatus.

2. The replacement cassette according to claim 1, wherein the recess of the coupling element is at least partially circumferential.

3. The replacement cassette according to claim 2, wherein the recess is formed over more than 180° of the coupling element.

4. The replacement cassette according to claim 1, wherein the recess is formed with a chamfer.

5. The replacement cassette according to claim 1,
wherein the recess is designed and arranged for direct engagement of prongs of the fork-shaped arm, and
wherein the fork-shaped arm including a plate and one or more strain gauges provided on the plate, the prongs being formed on the plate.

6. The replacement cassette according to claim 1, wherein the recess in the coupling element is oriented substantially parallel to the membrane.

7. The replacement cassette according to claim 1, wherein the membrane and the coupling element are formed in one piece.

8. The replacement cassette according to claim 1, wherein
the hard region is made of a thermoplastic, including polypropylene (PP) or polyethylene (PE),
the soft region is made of a thermoplastic elastomer (TPE), and
the hard region and the soft region are formed as an integral multi-component injection-molded part.

9. The replacement cassette according to claim 1, wherein the at least one hard region is made of a hard plastic, and the at least one soft region is made of a soft plastic.

10. The replacement cassette according to claim 1, wherein the at least one soft region forms seals of the pressure chamber and/or the liquid channels.

11. The replacement cassette according to claim 1, wherein the at least one soft region includes soft regions forming functional elements of the replacement cassette, and the functional elements form
a squeeze pump region for liquid in the liquid channels,
a valve arrangement region for varying a flow cross-section in at least one of the liquid channels,
a positive pressure sensor region for determining a liquid pressure in at least one of the liquid channels, and/or
a passive, flexible ripple compensation region for balancing pressure and/or volume fluctuations of a liquid delivery by means of an elastic liquid channel region.

12. The replacement cassette according to claim 1, further comprising:
a flange connection for connection of a container for providing infusion liquid,
an infusion connection for feeding the infusion liquid to the ophthalmic apparatus,
an aspiration connection for connection of at least one of the liquid channels to the ophthalmic apparatus,
a waste connection for discharging liquid into a waste container, and/or
an infusion valve,
wherein a liquid channel of the liquid channels connected to the aspiration connection is connected to the pressure detection arrangement.

13. The replacement cassette according to claim 1, wherein the hard region has recesses, by which regions of the replacement cassette which are formed from the soft region are mechanically accessible from outside the replacement cassette.

14. The replacement cassette according to claim 9, wherein the replacement cassette is constructed with:
a first outer shell and a second outer shell, each formed from two-component injection molding of the hard plastic and the soft plastic, which form the housing of the replacement cassette, and
a core part made of the hard plastic, wherein
the core part is arranged between the first outer shell and the second outer shell,
the first outer shell and second outer shell and/or the core part are snapped or cold-pressed with one another to form the replacement cassette, and
the coupling element of the pressure detection arrangement protrudes beyond one of the first outer shell and the second outer shell at least in part.

15. The replacement cassette according to claim 7, wherein the membrane and the coupling element are formed from the same material.

16. The replacement cassette according to claim 11, wherein the squeeze pump region is for a volume delivery in a form of a peristaltic pump.

17. A replacement cassette configured for at least partially inserted into an ophthalmological apparatus in an interchangeable manner, the replacement cassette comprising:
at least one hard region as housing of the replacement cassette; and
at least one soft region,
wherein the at least one hard region and the at least one soft region form inner liquid channels of the replacement cassette, and
wherein the at least one soft region forms a cassette-side pressure detection arrangement for determining a liquid pressure in at least one of the liquid channels,
wherein the pressure detection arrangement is formed in the replacement cassette and comprises a flexible membrane and a coupling element,
the flexible membrane defining an outer wall of a pressure chamber, which is connected to the at least one of the liquid channels,
the coupling element protruding outwardly with respect to the pressure chamber, and
the flexible membrane peripherally surrounding the coupling element,
wherein the coupling element is formed with a recess in such a way that, as the replacement cassette is inserted substantially parallel to the membrane into the ophthalmological apparatus, a fork-shaped arm of a force measuring arrangement of the ophthalmological apparatus engages in the recess substantially parallel to the membrane in such a way that the coupling element is surrounded at least on two sides by the fork-shaped arm and a force effect on the membrane occurring in a direction substantially normal in relation to the membrane is detectable by the force measuring arrangement both in a positive and in a negative direction, and
wherein the coupling element is formed with the recess in such a way that two prongs of the fork-shaped arm are receivable in the recess of the coupling element in such a way that the coupling element at the recess is surrounded by the prongs on at least three sides.

18. A replacement cassette configured for at least partially inserted into an ophthalmological apparatus in an interchangeable manner, the replacement cassette comprising:
   at least one hard region as housing of the replacement cassette; and
   at least one soft region,
      wherein the at least one hard region and the at least one soft region form inner liquid channels of the replacement cassette, and
      wherein the at least one soft region forms a cassette-side pressure detection arrangement for determining a liquid pressure in at least one of the liquid channels,
   wherein the pressure detection arrangement is formed in the replacement cassette and comprises a flexible membrane and a coupling element,
      the flexible membrane defining an outer wall of a pressure chamber, which is connected to the at least one of the liquid channels,
      the coupling element protruding outwardly with respect to the pressure chamber, and
      the flexible membrane peripherally surrounding the coupling element,
   wherein the coupling element is formed with a recess in such a way that, as the replacement cassette is inserted substantially parallel to the membrane into the ophthalmological apparatus, a fork-shaped arm of a force measuring arrangement of the ophthalmological apparatus engages in the recess substantially parallel to the membrane in such a way that coupling element is surrounded at least on two sides by the fork-shaped arm and a force effect on the membrane occurring in a direction substantially normal in relation to the membrane is detectable by the force measuring arrangement both in a positive and in a negative direction,
   wherein the recess of the coupling element is at least partially circumferential, and
   wherein the recess extends over three sides of the coupling element.

19. The replacement cassette according to claim 18, wherein the recess is formed in such a way as to receive the fork-shaped arm over an angular range of more than 180°.

* * * * *